(12) United States Patent
Kim et al.

(10) Patent No.: US 11,864,967 B2
(45) Date of Patent: Jan. 9, 2024

(54) PACKAGING CONTAINER FOR DENTAL IMPLANT

(71) Applicant: DIO Corporation, Busan (KR)

(72) Inventors: Jin Cheol Kim, Yangsan-si (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 500 days.

(21) Appl. No.: 17/267,220

(22) PCT Filed: Jul. 17, 2019

(86) PCT No.: PCT/KR2019/008811
§ 371 (c)(1),
(2) Date: Feb. 9, 2021

(87) PCT Pub. No.: WO2020/045824
PCT Pub. Date: Mar. 5, 2020

(65) Prior Publication Data
US 2021/0307889 A1  Oct. 7, 2021

(30) Foreign Application Priority Data

Aug. 28, 2018 (KR) .......................... 10-2018-0101046
Oct. 19, 2018 (KR) .......................... 10-2018-0124922
Dec. 17, 2018 (KR) .......................... 10-2018-0163054

(51) Int. Cl.
*A61C 19/02* (2006.01)
*A61C 8/00* (2006.01)
(Continued)

(52) U.S. Cl.
CPC ............ *A61C 19/02* (2013.01); *A61C 8/0087* (2013.01); *A61L 2/10* (2013.01); *A61L 2/202* (2013.01);
(Continued)

(58) Field of Classification Search
CPC ...... A61B 17/865; A61B 50/30; A61C 8/0087; A61C 8/0089; A61C 19/02; A61L 2/10;
(Continued)

(56) References Cited

U.S. PATENT DOCUMENTS 5,062,800 A * 11/1991 Niznick ............... A61C 8/0087
433/229
5,368,160 A * 11/1994 Leuschen ............. A61C 8/0087
206/339
(Continued)

FOREIGN PATENT DOCUMENTS

KR   10-0723949   6/2007
KR   10-0886400   3/2009
(Continued)

*Primary Examiner* — Gideon R Weinerth
(74) *Attorney, Agent, or Firm* — LEX IP MEISTER, PLLC

(57) ABSTRACT

The present disclosure provides a dental implant packaging container including: a see-through body unit in which upper and lower sides are open to form an accommodation space so that a dental implant fixture is accommodated therein and which is made of a material through which UV light for surface modification passes; a first cap unit which includes a hollow first cap body configured to cover an upper end portion of the accommodation space, a first fixing part protruding from a lower portion of the first cap body and having a coupling surface formed on an outer side portion, and a protruding part provided to protrude from the first fixing; a hollow holder unit which has an outer circumferential portion coupled to an inner circumference of the see-through body unit and an inner circumferential portion coupled to the coupling surface to mediate the connection between the see-through body unit and the first cap unit; and a second cap unit which includes a second fixing part fitted and coupled to a lower end portion of the see-through body unit and a base part provided on an inner side end of the (Continued)

second fixing part so that a lower end portion of the fixture is seated thereon.

18 Claims, 18 Drawing Sheets

(51) Int. Cl.
  *A61L 2/10* (2006.01)
  *A61L 2/20* (2006.01)
(52) U.S. Cl.
  CPC ..... *A61L 2202/122* (2013.01); *A61L 2202/21* (2013.01); *A61L 2430/12* (2013.01)
(58) Field of Classification Search
  CPC .... A61L 2/202; A61L 2/0047; A61L 2202/00; A61L 2202/122; A61L 2202/21; A61L 2202/182; A61L 2202/23; A61L 2202/24; A61L 2430/12
  USPC ....... 206/368, 63.5, 339; 433/172, 173, 174, 433/141
  See application file for complete search history.

(56) References Cited

U.S. PATENT DOCUMENTS

| | | | | | |
|---|---|---|---|---|---|
| 5,538,428 | A | * | 7/1996 | Staubli | A61C 8/0087 206/63.5 |
| 5,558,230 | A | * | 9/1996 | Fischer | A61C 8/0087 206/570 |
| 5,622,500 | A | * | 4/1997 | Niznick | A61C 8/0087 206/63.5 |
| 5,733,124 | A | * | 3/1998 | Kwan | A61C 8/0024 433/173 |
| 5,755,575 | A | * | 5/1998 | Biggs | A61C 8/0087 206/63.5 |
| 6,217,332 | B1 | * | 4/2001 | Kumar | A61C 8/0087 433/173 |
| 6,247,932 | B1 | * | 6/2001 | Sutter | A61C 8/0087 433/173 |
| 6,280,192 | B1 | * | 8/2001 | Groll | A61C 8/0087 206/63.5 |
| 6,416,324 | B1 | * | 7/2002 | Day | A61C 8/008 433/173 |
| 6,464,500 | B1 | * | 10/2002 | Popovic | A61C 8/0022 433/173 |
| 6,561,805 | B2 | * | 5/2003 | Kumar | A61C 8/0089 206/368 |
| D731,169 | S | * | 6/2015 | Sakaguchi | D3/203.1 |
| 11,166,780 | B2 | * | 11/2021 | Richart | A61B 17/865 |
| 11,723,756 | B2 | * | 8/2023 | Kunz | A61C 8/0087 206/63.5 |
| 2002/0025505 | A1 | * | 2/2002 | Beaty | A61C 8/0001 433/141 |
| 2003/0221977 | A1 | * | 12/2003 | Kumar | A61C 8/0087 206/63.5 |
| 2004/0043358 | A1 | * | 3/2004 | Howlett | A61C 8/0087 433/141 |
| 2005/0023166 | A1 | * | 2/2005 | Howlett | A61C 8/0087 206/369 |
| 2005/0287045 | A1 | * | 12/2005 | Levisman | B65D 77/0493 422/408 |
| 2006/0243616 | A1 | * | 11/2006 | Caron | A61B 50/30 206/349 |
| 2007/0181446 | A1 | * | 8/2007 | Donahoe | A61C 8/0087 206/63.5 |
| 2009/0065387 | A1 | * | 3/2009 | Bammerlin | A61C 8/0087 206/368 |
| 2011/0247947 | A1 | * | 10/2011 | Nihei | A61C 8/0087 206/63.5 |
| 2013/0065197 | A1 | * | 3/2013 | Mamraev | A61C 8/0087 433/172 |
| 2013/0167873 | A1 | * | 7/2013 | Ogawa | A61L 2/10 134/18 |
| 2013/0189642 | A1 | * | 7/2013 | Ogawa | A61L 2/10 433/29 |
| 2013/0264495 | A1 | * | 10/2013 | Ogawa | A61L 2/0047 250/455.11 |
| 2014/0042050 | A1 | * | 2/2014 | Richart | A61F 2/0095 206/438 |
| 2014/0127645 | A1 | * | 5/2014 | Goldenberg | A61B 17/86 606/301 |
| 2014/0166508 | A1 | * | 6/2014 | Richard | A61C 8/0087 206/63.5 |
| 2014/0166509 | A1 | * | 6/2014 | Chung | A61C 8/0087 206/205 |
| 2014/0202892 | A1 | * | 7/2014 | Thome | A61C 8/0087 206/63.5 |
| 2016/0361150 | A1 | * | 12/2016 | Berndt | A61L 2/14 |
| 2017/0095308 | A1 | * | 4/2017 | Roesler | A61B 50/30 |
| 2019/0159874 | A1 | * | 5/2019 | Jung | A61C 8/005 |
| 2020/0275999 | A1 | * | 9/2020 | Chelminski | A61C 8/0087 |
| 2020/0367996 | A1 | * | 11/2020 | Berner | A61L 2/14 |
| 2021/0077242 | A1 | * | 3/2021 | Agarwal | A61B 50/00 |
| 2021/0307889 | A1 | * | 10/2021 | Kim | B65D 81/24 |
| 2021/0361392 | A1 | * | 11/2021 | Ju | A61C 19/06 |
| 2022/0409346 | A1 | * | 12/2022 | Wu | A61C 8/0087 |
| 2023/0052702 | A1 | * | 2/2023 | Momany | A61B 50/30 |
| 2023/0263603 | A1 | * | 8/2023 | Zastrow | A61C 8/0089 433/173 |

FOREIGN PATENT DOCUMENTS

| | | | | |
|---|---|---|---|---|
| KR | 20110024641 A | * | 3/2011 | ............ A61J 1/06 |
| KR | 10-2011-0114487 | | 10/2011 | |
| KR | 101394116 | * | 5/2014 | ............ A61C 19/02 |
| KR | 10-1439344 | | 9/2014 | |
| KR | 101511332 B1 | * | 4/2015 | ............ A61J 1/06 |
| KR | 10-2016-0058071 | | 5/2016 | |
| KR | 10-1797158 | | 11/2017 | |

\* cited by examiner

PACKAGING CONTAINER FOR DENTAL IMPLANT

TECHNICAL FIELD

The present disclosure relates to a dental implant packaging container, and more particularly, to a dental implant packaging container allowing a fixture, of which a surface is irradiated with ultraviolet (UV) light so as to be modified, to be easily withdrawn without being contaminated so that convenience of use thereof is improved.

BACKGROUND ART

Generally, an implant refers to a replacement that substitutes for a human tissue when an original human tissue is lost. In dentistry, an implant refers to a fixture that substitutes for a dental root of a lost tooth, a crown that substitutes for a dental crown, an abutment that mediates between the fixture and the crown, a separately-placed denture, or the like. Also, surgery to restore the original function of a tooth may be performed using the implant.

Here, in order to prevent the infection of tissues in the oral cavity, such as an alveolar bone, due to contamination caused by foreign matter, bacteria, or the like during the placement of an implant such as the fixture, the implant is treated to inhibit bacterial growth and then stored in sealed packaging.

Also, currently, most fixtures are treated to have a hydrophilic surface through the process of resorbable blast media (RBM), sandblasting/large-grit/acid etching (SLA), or the like. At this time, when the surface of the fixture is exposed to air after the process, as time passes, an oxidized layer increases and surface energy is stabilized due to contaminants such as hydrocarbon compounds, and the surface of the fixture turns hydrophobic.

Accordingly, as the period of osseointegration is increased due to the decrease in hydrophilicity with respect to body fluids and blood, there is a problem in that the recovery period until the implant is stabilized increases.

Meanwhile, some products including a storage container that allows the hydrophilicity of the fixture with a modified surface to be maintained for a long period have been launched. However, since fixtures including such storage containers are expensive, there is a problem in that a financial burden is imposed on consumers. Moreover, since consumers have to use products of specific companies despite their high cost, there is a problem in that the consumers have a very narrow range of choices.

In order to address such problems, in recent years, some ultraviolet (UV) light irradiation devices for surface treatment have been disclosed that are able to, after a fixture is mounted therein, irradiate a surface of the fixture with UV light to modify the surface of the fixture and also remove organic contaminants adhering to the surface. Here, the conventional UV light irradiation devices for surface treatment perform sterilization treatment prior to the surface modification of the fixture.

Conventionally, Korean Unexamined Patent Application Publication No. 10-2014-0125764 (Title of Invention: Method of enhancing soft tissue integration and sealing around prosthetic devices) has disclosed that soft tissue integration and sealing are enhanced by about 10% or more when a prosthetic device treated with UV light is used as compared to when a prosthetic device not treated with UV light is used.

However, since a container in which the fixture is packaged, onto which UV light is projected, is colored in the process of sterilization treatment, there is a problem in that the fixture is not able to be smoothly irradiated with UV light for surface modification treatment.

Meanwhile, in the process of surface modification treatment, when the container in which the fixture is packaged is irradiated with UV light, oxygen remaining in the container is converted to ozone. Also, as carbon atoms deposited on the surface of the fixture combine with the ozone and are separated from the surface of the fixture, the surface of the fixture is changed from hydrophobic to hydrophilic.

However, since conventional packaging containers, in which fixtures are packaged, are sealed, the amount of oxygen remaining in the container is not sufficient for the process in which the fixture is irradiated with UV light to modify the surface of the fixture, and accordingly, the amount of oxygen converted to ozone is not sufficient. Thus, there is a problem in that surface modification capability is degraded and osseointegration is not able to be stably performed.

Further, the conventional packaging containers have a problem in that, since an end portion of the fixture is hidden from UV light due to a portion supporting the fixture when the fixture is irradiated with UV light, the surface modification and sterilization treatment are not able to be performed on the end portion of the fixture.

In addition, when the fixture, on which the surface modification treatment is performed, is attempted to be withdrawn from the conventional containers, since the fixture is not supported and falls to an inner surface of the container, the fixture is contaminated. Thus, since the fixture has to be surface-treated and sterilized again, there is a problem in that the overall dental implant placement process is delayed.

DISCLOSURE

Technical Problem

The present disclosure is directed to providing a dental implant packaging container allowing a fixture, of which a surface is irradiated with ultraviolet (UV) light so as to be modified, to be easily withdrawn without being contaminated so that convenience of use thereof is improved.

Technical Solution

One aspect of the present disclosure provides a dental implant packaging container including: a see-through body unit in which upper and lower sides are open to form an accommodation space so that a dental implant fixture is accommodated therein and which is made of a material through which UV light for surface modification passes; a first cap unit which includes a hollow first cap body configured to cover an upper end portion of the accommodation space, a first fixing part protruding from a lower portion of the first cap body and having a coupling surface formed on an outer side portion, and a protruding part provided to protrude from the first fixing part so as to be inserted into an inner circumferential fastening groove of the fixture; a hollow holder unit which has an outer circumferential portion coupled to an inner circumference of the see-through body unit and an inner circumferential portion coupled to the coupling surface to mediate the connection between the see-through body unit and the first cap unit; and a second cap unit which includes a second fixing part fitted and coupled to a lower end portion of the see-through body unit and a base part provided on an inner side end of the second fixing part so that a lower end portion of the fixture is seated thereon.

Advantageous Effects

The present disclosure provides the following advantageous effects.

First, since a coupling surface on an outer side portion of a first fixing part formed in the shape of a bar that crosses a hollow at an inner circumference of a first cap unit is coupled with a minimum contact area to an inner circumferential portion of a hollow holder unit, in order to withdraw a fixture, of which a surface is modified, without causing contamination thereof, the first cap unit can be removed in a state in which the holder unit is coupled to a see-through body unit. Therefore, convenience of use can be significantly improved.

Second, since an outer circumferential portion of the holder unit that is in close contact with an inner circumference of the see-through body unit and forcibly fitted and coupled thereto is provided to be stepped outward in a radial direction, and a radius of the outer circumferential portion is decreased downward from the step so that the outer circumferential portion is inclined inward in the radial direction, a frictional fixing force is increased in a withdrawal direction, and thus a state in which the holder unit and the see-through body unit are coupled can be maintained even when the first cap unit is removed.

Third, since UV transmission gaps are formed at a plurality of sites in a circumferential direction, and thus an upper end portion of the fixture is supported while a region of the fixture that is hidden from UV light due to a bushing part coupled to a lower end of the holder unit is minimized, surface modification capability can be improved, and contamination of the fixture due to the fixture falling into an accommodation space can be prevented.

Fourth, since a separation space formed between a cutting surface on a side surface of a second fixing part, which is formed to cross a hollow at an inner circumference of a second cap unit, and the inner circumference of the see-through body unit communicates with the outside and the accommodation space, the flow of oxygen for ozone generation is sufficiently formed on the fixture which is subject to surface modification, and thus surface modification performance can be improved.

[Best Mode of the Invention]

The best mode of the present disclosure will be described in more detail below with reference to the accompanying drawings.

[Modes of the Invention]

Hereinafter, a dental implant packaging container according to an exemplary embodiment of the present disclosure will be described in detail with reference to the accompanying drawings.

Figure 1:
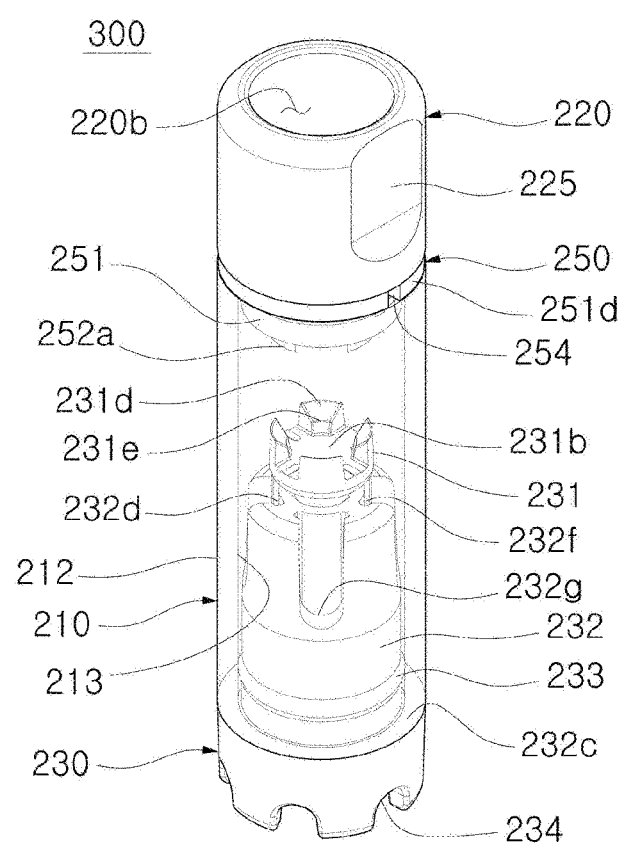
FIG. 1 is a perspective view of a dental implant packaging container according to a first embodiment of the present disclosure in which the inside of the dental implant packaging container is visible.
Figure 2:
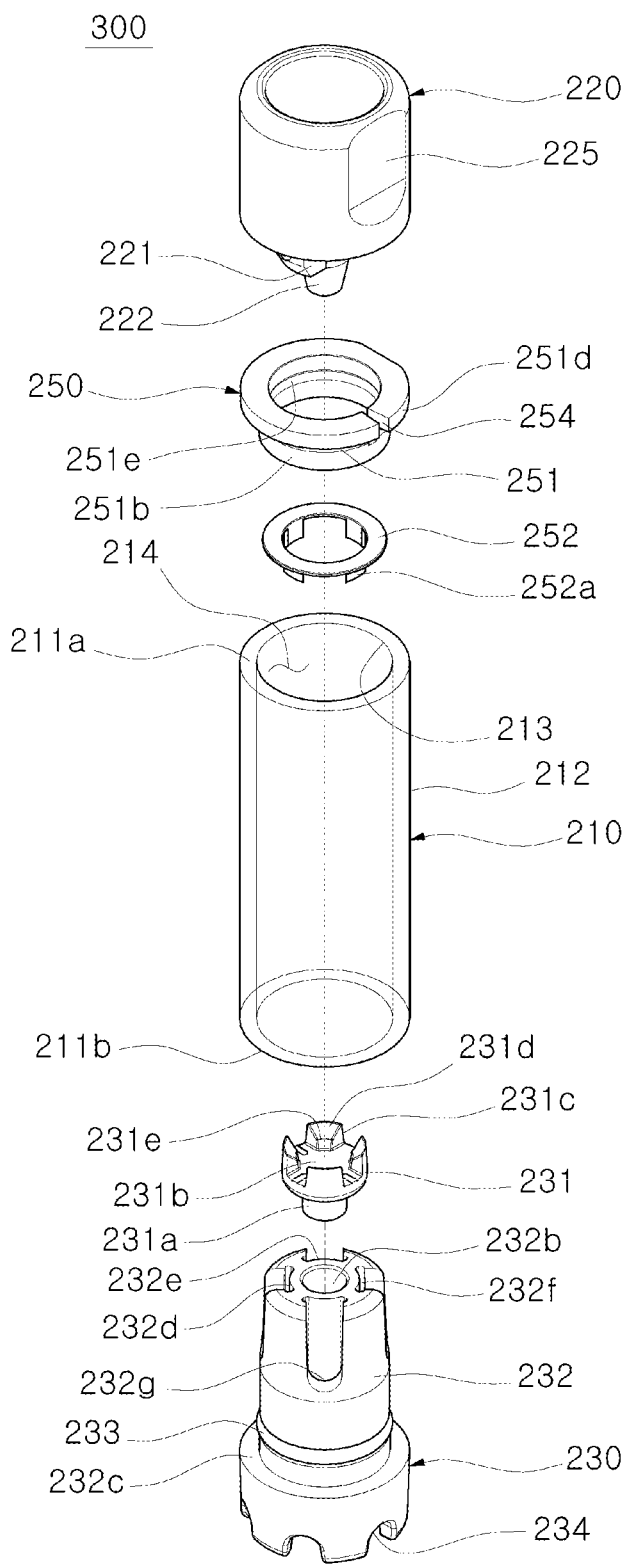
FIG. 2 is an exploded perspective view of the dental implant packaging container according to the first embodiment of the present disclosure.

FIG. 1 is a perspective view of a dental implant packaging container according to a first embodiment of the present disclosure in which the inside of the dental implant packaging container is visible, and FIG. 2 is an exploded perspective view of the dental implant packaging container according to the first embodiment of the present disclosure.

Figure 3:
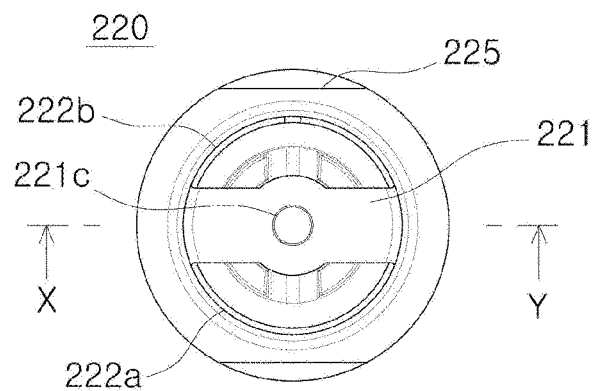
FIG. 3 is a top view of the dental implant packaging container according to the first embodiment of the present disclosure.
Figure 4A:
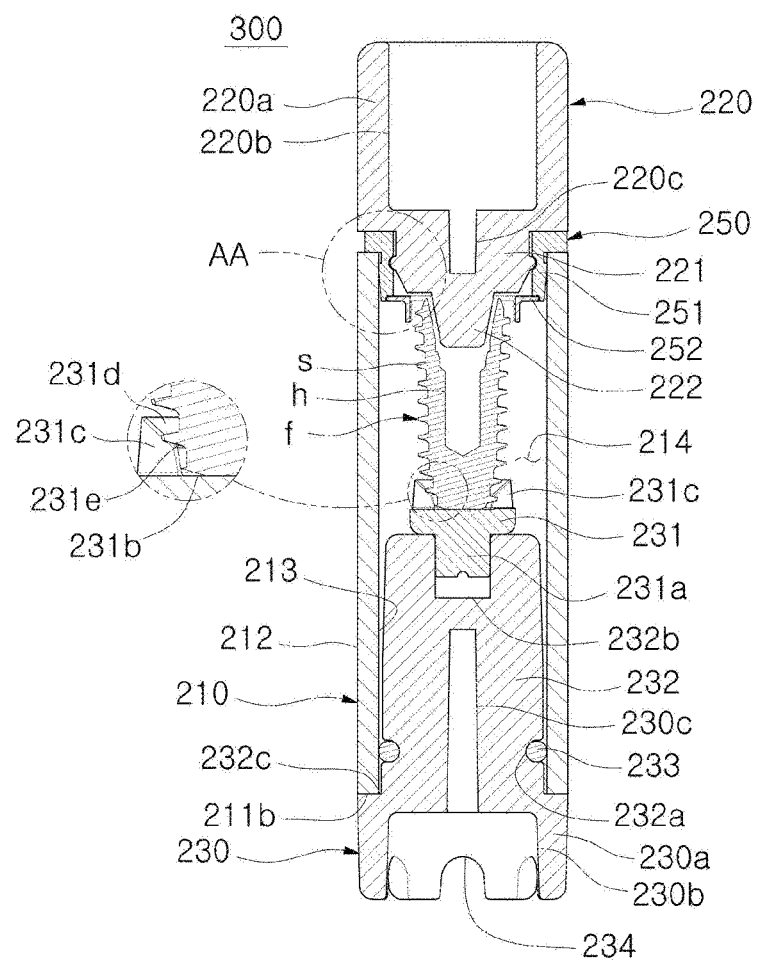
FIG. 4A is a cross-sectional view taken along line X-Y of FIG. 3.
Figure 4B:
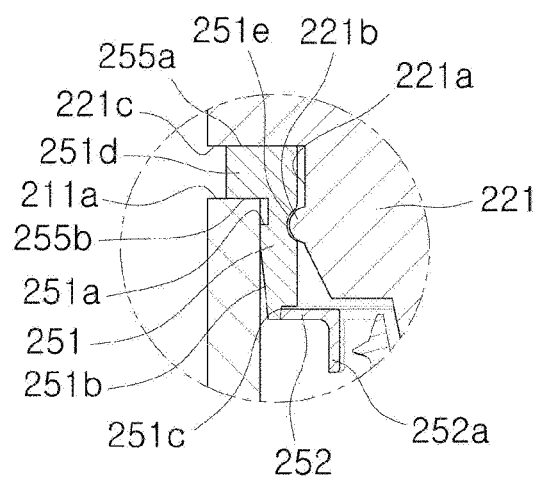
FIG. 4B is an enlarged view of portion AA of FIG. 4A.
Figure 5:
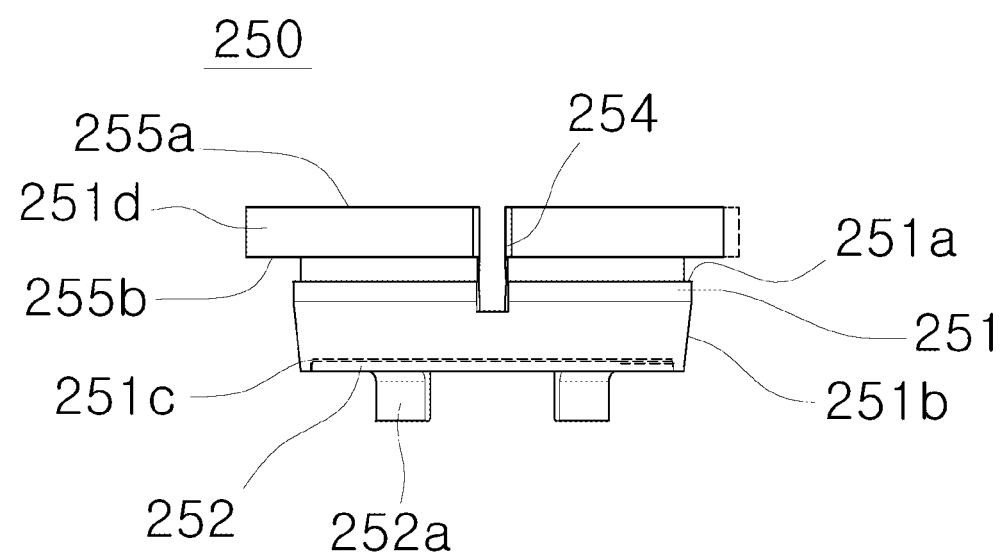
FIG. 5 is a lateral exemplary view illustrating a holder unit and a bushing support part of the dental implant packaging container according to the first embodiment of the present disclosure.
Figure 6:
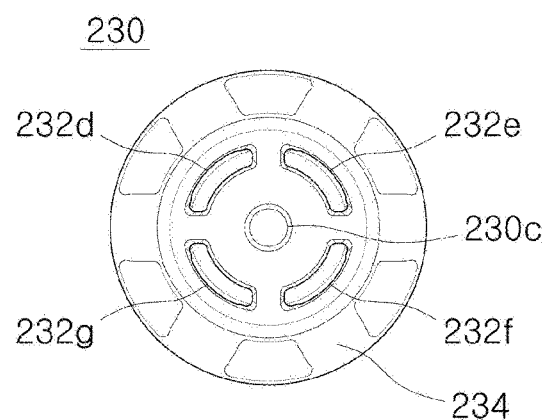
FIG. 6 is a bottom view of the dental implant packaging container according to the first embodiment of the present disclosure.
Figure 7:
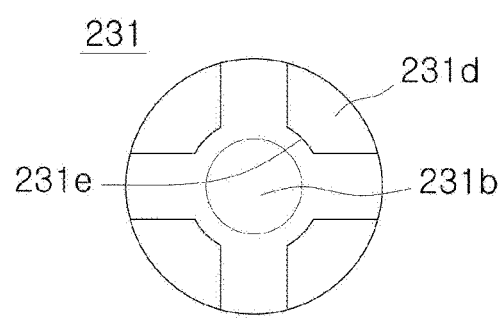
FIG. 7 is a top view illustrating a base part of the dental implant packaging container according to the first embodiment of the present disclosure.

Also, FIG. 3 is a top view of the dental implant packaging container according to the first embodiment of the present disclosure, FIG. 4A is a cross-sectional view taken along line X-Y of FIG. 3, and FIG. 4B is an enlarged view of portion AA of FIG. 4A. Also, FIG. 5 is a lateral view illustrating a holder unit and a bushing support part of the dental implant packaging container according to the first embodiment of the present disclosure, and FIG. 6 is a bottom view of the dental implant packaging container according to the first embodiment of the present disclosure. Also, FIG. 7 is a top view illustrating a base part of the dental implant packaging container according to the first embodiment of the present disclosure.

As shown in FIGS. 1 to 7, a dental implant packaging container 300 according to the first embodiment of the present disclosure includes a see-through body unit 210, a first cap unit 220, a second cap unit 230, and a holder unit 250.

Here, the see-through body unit 210 may have open upper and lower sides to form an accommodation space 214 so that a dental implant fixture f is accommodated therein and may be made of a material through which ultraviolet (UV) light for surface modification of the fixture f passes. At this time, the see-through body unit 210 may have an outer circumferential surface 212 and an inner circumferential surface 213 formed with a predetermined thickness in a radial direction and may be provided to be hollow.

Also, the see-through body unit 210 may be provided in various shapes such as a cylindrical shape and a polygonal column shape, and the holder unit 250 and the second cap unit 230 may be detachably coupled to both end portions of the see-through body unit 210. Also, in order to prevent loss, damage due to falling, and the like due to a user's mistake, the see-through body unit 210 may be provided to have a cross-section in the form of a water droplet that has one circumferential side protruding outward in the radial direction from a circular cross-section.

At this time, a first edge 211a and a second edge 211b may be formed on edges of both ends of the see-through body unit 210 in a longitudinal direction thereof so as to come in contact with the holder unit 250 and the second cap unit 230, respectively. Here, it may be understood that the first edge 211a is formed on one side end of the see-through body unit 210, and the second edge 211b is formed on the other side end of the see-through body unit 210. Also, the first edge 211a and the second edge 211b may be formed with a predetermined thickness in the radial direction.

Meanwhile, the accommodation space 214 may be formed inside the see-through body unit 210 to accommodate the dental implant fixture f on which first surface modification and sterilization treatment are performed. At this time, the accommodation space 214 may be open so as to vertically pass through the see-through body unit 210. Accordingly, oxygen for surface modification of the fixture f may enter the see-through body unit 210 and be stored therein.

Also, the accommodation space 214 may be formed to have an inner diameter that exceeds the maximum outer diameter portion of the fixture f so that the fixture f is inserted into and withdrawn from the accommodation space 214, and a vertical length of the accommodation space 214 may be formed to exceed a vertical length of the fixture f. That is, it may be understood that the see-through body unit 210, in which the inner circumferential surface 213 is formed, is formed to have an inner diameter that exceeds an outer diameter of the maximum outer diameter portion of the fixture f in the radial direction. Also, it may be understood that a vertical length of the see-through body unit 210 is formed to exceed the vertical length of the fixture f.

Meanwhile, a screw portion s configured to be inserted into an alveolar bone of a subject may be formed on an outer surface of the fixture f, and an inner circumferential fastening groove h may be formed to be recessed in an upper portion of the fixture f so that a dental implant abutment is coupled thereto. At this time, a tooth-shaped crown may be coupled to an upper portion of the abutment.

Here, the fixture f may be made of a metal material, such as titanium, which has high strength, excellent corrosion resistance, and biocompatibility. Also, the first surface modification treatment may be performed on the fixture f so that the outer surface of the fixture f and the screw portion s have hydrophilicity with respect to body fluids and blood. Also, in order to prevent infection during placement of the fixture f, first sterilization treatment may be performed on the fixture f, and then the fixture f may be accommodated in the accommodation space 214.

For example, the fixture f may be surface-treated by resorbable blast media (RBM) in which biocompatible media, such as aluminum oxide, titanium oxide and calcium phosphate, are ejected onto the surface to form roughness. Also, after the surface treatment by RBM, the first surface modification treatment may be performed on the fixture f through sandblasting/large-grit/acid etching (SLA) surface treatment in which chemical etching is performed using acid solution or the like. In addition, the fixture f may be exposed to a cleaning solution, UV light, plasma, ozone, and the like so that the first sterilization treatment is performed thereon.

Accordingly, since the first sterilization treatment is performed on the fixture f, side effects such as infection and inflammation may be minimized during placement of the fixture f, and the placed fixture f may be stably osseointegrated.

Meanwhile, since the see-through body unit 210 is made of a quartz material whose extinction coefficient is lower than that of a generally-used container made of glass or a transparent synthetic resin material, UV transmittance may significantly increase, and the sterilizing power of UV light may be preserved. Specifically, the surface of the fixture f is irradiated with UV light as the UV light is irradiated from a separately-provided UV light irradiation device, passes through the see-through body unit 210 made of quartz material, and substantially passes through the accommodation space 214.

Accordingly, since the UV light is irradiated from the UV light irradiation device and passes through the see-through body unit 210 and the accommodation space 214 is substantially irradiated with the UV light, the ability to modify the surface of the fixture f and the ability to sterilize and clean the surface of the fixture f may be significantly improved. Further, since the see-through body unit 210 is made of the quartz material having a low extinction coefficient, coloration of the see-through body unit 210 may be prevented, the UV light for surface modification treatment may pass through the see-through body unit 210, and the fixture f may be irradiated with the UV light.

Here, the UV light irradiation device may emit UV light having a wavelength in a range of 150 nm to 400 nm. At this time, when a wavelength range of light emitted from the UV light irradiation device is less than 150 nm, due to excessive energy, a skin tissue may be damaged when exposed to the UV light. Also, when the wavelength range of light emitted from the UV light irradiation device exceeds 400 nm, substantial sterilization and surface modification effects may be insufficient.

At this time, the UV light may be classified into UV-V, UV-C, UV-B, and UV-A according to the wavelength range. That is, UV-V refers to UV light having a wavelength in a range of 100 nm to 200 nm, UV-C refers to UV light having a wavelength in a range of 200 nm to 280 nm, UV-B refers to UV light having a wavelength in a range of 280 nm to 315 nm, and UV-A refers to UV light having a wavelength in a range of 315 nm to 400 nm. The shorter the wavelength, the higher the energy.

Here, oxygen molecules may be converted to ozone, which is a reactive generator, as outer-shell electrons of the oxygen molecules are excited through energy bombardment exceeding the binding energy of the oxygen molecules by the UV light. Specifically, the surface of the fixture f may be converted to a high-energy-state hydrophilic surface having an —OH functional group through the first surface modification treatment. At this time, the formed —OH functional group may bind with carbon and may be stabilized over time, and the surface of the fixture f may be converted to a low-energy-state hydrophobic surface.

At this time, the ozone generated through the UV light may combine with carbon atoms deposited on the surface of the fixture f such that the carbon atoms are separated from the surface of the fixture f, and accordingly, the surface of the fixture f may be converted to the high-energy-state hydrophilic surface again.

Accordingly, a large amount of hydroxyl groups may be supplied to the air inside the accommodation space 214, and the amount of ozone generated through UV light may be increased. Therefore, since the carbon-based contaminants deposited on the surface of the fixture f are separated and removed through the reaction with ozone, the fixture f may be stably stored in a state in which the surface thereof is modified.

Also, since a photocatalytic reaction in which carbon atoms are separated from the biocompatible media, such as titanium oxide, on the surface of the fixture f is activated due to the supplied hydroxyl groups, the efficiency of second surface modification of the fixture f through UV light may be significantly improved.

In addition, since binding rings of organic materials on the surface of the fixture f are broken due to UV light with which the surface of the fixture f is irradiated, a surface cleaning effect may be imparted, and a sterilization effect may be provided due to viruses and bacteria being removed.

Meanwhile, the first cap unit 220 may include a hollow first cap body 220a configured to cover an upper end portion of the accommodation space 214, a first fixing part 221 protruding from a lower portion of the first cap body 220a and having a coupling surface 221a formed on an outer side portion, and a protruding part 222 provided to protrude from the first fixing part 221 so as to be inserted into the inner circumferential fastening groove h of the fixture f.

Here, the first cap unit 220 may be provided in a cylindrical shape or the like to correspond to the shape of the see-through body unit 210, and a hollow 220b may be formed to vertically pass through a radially inner central portion of the first cap unit 220. At this time, a D-cut portion 225 may be formed on one side of an outer circumference of the first cap unit 220, and in some cases, a plurality of first recessed groove portions (not illustrated) may be formed to be recessed at predetermined intervals along a circumferential direction in an upper end portion of the first cap unit 220.

Accordingly, since the D-cut portion 225 is formed to have a flat surface on one side of the outer circumference of first cap unit 220, when inserting the dental implant packaging container 300 into a separate UV light irradiation device or the like, the dental implant packaging container 300 may be easily mounted using tweezers or the like. Also, since the first recessed groove portions (not illustrated) are formed to be recessed at predetermined intervals along the circumferential direction in the upper end portion of the first cap unit 220, the dental implant packaging container 300 may be supported and fixed in an upright state in an external fixing device or the like. Therefore, convenience of use may be improved.

Also, the first cap unit 220 may be made of materials such as a synthetic resin. In order to allow UV light for surface modification of the fixture f to pass through the first cap unit 220, the first cap unit 220 may be made of a synthetic resin material such as a transparent or semi-transparent polycarbonate material.

Also, a first support step 221c that comes in contact with an upper surface of the holder unit 250 may be formed on an outer side of a lower end portion of the first cap unit 220. At this time, in the first cap unit 220, the first fixing part 221 may be integrally formed with the first support step 221c in a radially inward direction of the first support step 221c. That is, the first fixing part 221 may be formed to integrally extend and protrude downward from an inner side end at the lower portion of the first cap body 220a.

Specifically, the first fixing part 221 may be formed in the shape of a bar that crosses the hollow 220b of the first cap body 220a and may protrude downward, and the coupling surface 221a may be formed on an outer side portion of the first fixing part 221. At this time, in some cases, the first fixing part 221 may be formed in the shape of a cross that crosses the hollow 220b and may be integrally formed with the first cap body 220a.

Here, a length of the bar of the first fixing part 221 in the longitudinal direction thereof may be formed to be less than the inner diameter of the see-through body unit 210 and formed to substantially correspond to an inner diameter of the holder unit 250. At this time, an outer surface profile of the coupling surface 221a may be formed to be round so as to correspond to a round profile of an inner circumferential portion of the holder unit 250.

Accordingly, the coupling surface 221a on the outer side portion of the first fixing part 221, which is formed in the shape of a bar that crosses the hollow 220b of the first cap body 220a, is coupled with a minimum contact area to the inner circumferential portion of the holder unit 250. Accordingly, in order to withdraw the fixture f, whose surface is modified, without causing contamination thereof, the first cap unit 220 can be removed in a state in which the holder unit 250 is coupled to the see-through body unit 210. Therefore, convenience of use may be significantly improved.

Also, a catching protrusion 221b may be formed to extend and protrude outward in the radial direction from an outer circumference of the coupling surface 221a of the first fixing part 221. Also, in the inner circumferential portion of the holder unit 250, a catching groove 251e may be formed to be recessed at a position corresponding to the catching protrusion 221b so that the catching protrusion 221b is inserted into the catching groove 251e. Accordingly, when the first fixing part 221 is inserted into the inner circumferential portion of the holder unit 250, the catching protrusion 221b may be forcibly fitted into and coupled to the catching groove 251e in a detachable manner.

Also, on a lower side of the catching protrusion 221b of the first fixing part 221, a non-coupling surface may be formed with a diameter that decreases obliquely inward in the radial direction toward the lower end portion. Here, the non-coupling surface may be understood as an end surface formed on the lower end side of the outer side portion of the first fixing part 221. Also, the coupling surface 221a may be understood as an end surface that is formed between the first support step 221c and the catching protrusion 221b and formed to correspond to the profile of the inner circumferential portion of the holder unit 250. Also, in some cases, the first cap unit 220 and the holder unit 250 may be coupled to each other due to a fit-coupling force between the catching protrusion 221b and the catching groove 251e, without the coupling surface 221a coming in direct contact with the inner circumferential portion of the holder unit 250.

Accordingly, when the first fixing part 221 is inserted into the inner circumferential portion of the holder unit 250, a contact area therebetween is minimized Therefore, the coupling force between the first cap unit 220 and the holder unit 250 may be provided to be weaker than the coupling force between the holder unit 250 and the see-through body unit 210. In this way, even when the first cap unit 220 is separated from the holder unit 250, the state in which the holder unit 250 is coupled to the see-through body unit 210 may be maintained.

Also, at the lower central side of the first fixing part 221, the protruding part 222 may protrude and extend downward to be inserted into and caught in the inner circumferential fastening groove h of the fixture f. Here, the protruding part 222 may be formed in a shape in which a radial length decreases in a direction toward the lower end portion. At this time, an outer diameter of the protruding part 222 may be formed to correspond to an inner diameter of the inner circumferential fastening groove h of the fixture f or may be formed to be smaller than the inner diameter of the inner circumferential fastening groove h.

Accordingly, since the upper end portion of the fixture f is caught and supported through the protruding part 222 inserted into the inner circumferential fastening groove h of the fixture f, the fixture f may be prevented from falling into the accommodation space 214 of the see-through body unit 210. Therefore, as the first cap unit 220 is coupled to the holder unit 250 which is coupled to the see-through body unit 210, the fixture f may be irradiated with UV light and the surface of the fixture f may be modified in a state in which the fixture f is vertically arranged and fixed on the inner circumference of the see-through body unit 210.

Meanwhile, in the first cap unit 220, first through-passages 222a and 222b may be formed in a semi-circular shape at a plurality of sites between the inner circumference of the first cap body 220a and the first fixing part 221 so that the supply of oxygen for ozone generation for surface modification of the fixture f is concentrated thereto.

Here, each of the first through-passages 222a and 222b may be formed in the longitudinal direction of the first cap unit 220 and may communicate with the hollow 220b. Accordingly, even when the first cap unit 220 is coupled to the dental implant packaging container 300, external oxygen may flow through the hollow 220b and each of the first through-passages 222a and 222b.

Also, each of the first through-passages 222a and 222b may be formed to have a semi-circular cross-section between the inner circumferential surface of the first cap body 220a and the first fixing part 221. Accordingly, since the areas of the first through-passages, except for the areas thereof covered by the bar-shaped first fixing part 221, communicate with the hollow 220b and the areas of the passages are maximized such that the amount of oxygen flowing from the outside is increased, surface modification capability may be improved. Further, since the first through-passages 222a and 222b are formed to have a uniform size and the oxygen flowing into the see-through body unit 210 is uniformly distributed thereto, homogeneity may be secured during the surface modification of the fixture f.

Here, oxygen molecules, which are present inside the accommodation space 214 in which the fixture is disposed, may be converted to ozone, which is a reactive generator, as outer-shell electrons of the oxygen molecules are excited through energy bombardment exceeding the binding energy of the oxygen molecules. In this way, as carbon atoms deposited on the surface of the fixture f combine with the ozone and are separated from the surface of the fixture f, the surface of the fixture f may be converted from a lower-energy-state hydrophobic surface to a high-energy-state hydrophilic surface. At this time, when the fixture f is irradiated with UV light and the surface of the fixture f is modified in a state in which the see-through body unit 210 is sealed, there is a concern that the residual amount of oxygen may not be sufficient for the surface modification and the amount of oxygen converted to ozone may not be sufficient. Thus, there is a concern that, even when the fixture f is irradiated with UV light, the ability to modify the surface of the fixture f may be degraded and osseointegration may not be stably performed due to the lack of oxygen converted to ozone.

Therefore, as the first through-passages 222a and 222b are formed in the first cap unit 220, during irradiation with UV light, oxygen in the amount required for the surface modification process in the accommodation space 214 may be secured and may be converted to ozone. In this way, the ability to modify the surface of the fixture f using UV light may be improved, and since erosion and expansion of a surgical site, which occurs when a portion surrounding the fixture f is not modified to be hydrophilic, is prevented, osseointegration may be stably performed. Further, since the first fixing part 221 is disposed at the central portion while oxygen is supplied to the accommodation space 214 from the outside of the first through-passages 222a and 222b, foreign matter having a size larger than that of the first through-passages 222a and 222b may be blocked from being introduced into the accommodation space 214 from the outside.

Also, in the upper central side of the first fixing part 221, a first recessed portion 220c may be formed to be recessed downward and communicate with the hollow 220b. Accordingly, as a separate withdrawal device, whose shape matches the shape of the first recessed portion 220c, is inserted into the first recessed portion 220c, the first cap unit 220 may be separated from the holder unit 250 in the state in which the holder unit 250 is coupled to the see-through body unit 210.

Meanwhile, the holder unit 250 may be provided to mediate the connection between the see-through body unit 210 and the first cap unit 220 by having an outer circumferential portion coupled to the inner circumference of the see-through body unit 210 and an inner circumferential portion coupled to the coupling surface 221a.

Also, the holder unit 250 may be provided to have a hollow shape in which a central portion is open so that, even when the holder unit 250 is coupled to the see-through body unit 210, the fixture f may selectively pass through the central portion. At this time, the holder unit 250 may be provided to have a ring shape or the like of which a length corresponds to the diameter of the see-through body unit 210.

Here, the holder unit 250 may be made of a synthetic resin material such as a low-density polyethylene (LDPE) material, and in some cases, the holder unit 250 may be made of a metal material, such as titanium, which has high strength, excellent corrosion resistance, and biocompatibility.

Also, in the holder unit 250, a holder extension part 251 may be formed to protrude downward from an inner side end of a hollow body 251d, which is caught on the upper end of the see-through body unit 210 to be coupled to the inner circumference of the see-through body unit 210.

Here, the hollow body 251d at the upper portion of the holder unit 250 may be caught on the outer side of the upper end of the see-through body unit 210. Also, the holder extension part 251, which integrally extends and protrudes downward from the inner side end of the hollow body 251d, may be inserted into the inner circumference of the see-through body unit 210 and fitted and coupled thereto.

Accordingly, when the first cap unit 220 is removed in the state in which the holder unit 250 is coupled to the see-through body unit 210, the fixture f may be selectively inserted and withdrawn through the hollow of the holder unit 250.

Also, at one side of the upper portion of the holder unit 250, a clearance portion 254 may be formed to be open in the shape of a slit having a predetermined length in the circumferential direction. Specifically, when viewed from above, the upper end portion of the holder unit 250 may have a C-shape with an open one side. At this time, since the clearance portion 254 is not formed in the lower portion of the holder unit 250, when viewed from below, the lower end portion of the holder unit 250 may have a closed circular shape. Of course, in some cases, the clearance portion 254 may be provided to be vertically open throughout one side of the holder unit 250.

Here, even when the holder unit 250 is provided to be larger than the inner diameter of the see-through body unit 210, the clearance portion 254 may be narrowed and the holder unit 250 may be pressed from the C-shape to a shape close to a circular shape so that the holder unit 250 may be inserted into the inner circumference of the see-through body unit 210.

Accordingly, even when the outer diameter of the holder unit 250, in which the clearance portion 254 is formed to be open in the shape of a slit having a predetermined length in the circumferential direction at one side, is provided to have a size different from the inner diameter of the see-through body unit 210, the holder unit 250 and the see-through body unit 210 may be coupled to each other. Thus, compatibility may be improved.

Also, the outer circumferential portion of the holder unit 250 may protrude to be stepped outward in the radial direction and may be formed to be inclined inward in the radial direction toward the lower side so that a frictional fixing force is increased in the withdrawal direction.

Specifically, a catching step part 251a may protrude from the outer circumference of the holder extension part 251 so as to be stepped outward in the radial direction so that the frictional fixing force is increased in the withdrawal direction with respect to the see-through body unit 210. Also, a sliding coupling part 251b may be formed to extend from an outer circumferential surface of a lower side portion of the catching step part 251a so as to be inclined inward in the radial direction toward the lower side and fitted and fixed to the inner circumferential surface of the see-through body unit 210.

Here, the withdrawal direction refers to a direction from a lower side to an upper side in the longitudinal direction of the see-through body unit 210 when the holder unit 250 is coupled to the upper end portion of the see-through body unit 210 in the longitudinal direction thereof.

Accordingly, during insertion of the sliding coupling part 251b, which has a radius decreasing from the upper side to lower side so that the sliding coupling part 251b is inclined inward in the radial direction, into the see-through body unit 210, the holder extension part 251 with a gradually increasing radius may be fitted and coupled to the inner circumference of the see-through body unit 210. At this time, when the sliding coupling part 251b is fitted and coupled to the inner circumference of the see-through body unit 210, the entire end surface of the sliding coupling part 251b may be substantially brought into close contact with the inner circumferential surface of the see-through body unit 210 due to being fitted and coupled thereto. Also, during withdrawal of the sliding coupling part 251b from the see-through body unit 210, since the entire end surface of the sliding coupling part 251b is substantially brought into close contact with the inner circumferential surface of the see-through body unit 210, the holder unit 250 is not withdrawn from the see-through body unit 210 unless an external force of a predetermined magnitude or more is exerted on the holder unit 250 in the withdrawal direction.

Further, not only the contact area between the holder unit 250 and the see-through body unit 210 is wider than the contact area between the first cap unit 220 and the holder unit 250, but also the sliding coupling part 251b may slide to be fit-coupled to the inner circumference of the see-through body unit 210. Therefore, the coupling force between the holder unit 250 and the see-through body unit 210 may be provided to be larger than the coupling force between the first cap unit 220 and the holder unit 250, which are coupled while the contact area therebetween is minimized.

In this way, even when the first cap unit 220 is separated from the holder unit 250, the state in which the holder unit 250 is coupled to the see-through body unit 210 may be maintained. That is, the holder unit 250 coupled to the inner circumference of the see-through body unit 210 is not separated therefrom due to the external force that is applied when the first cap unit 220, which is fitted and coupled to the inner circumferential portion of the holder unit 250, is separated from the holder unit 250. Therefore, the frictional fixing force between the holder unit 250 and the see-through body unit 210 in the withdrawal direction is increased, and even when the first cap unit 220 is removed, the coupling state between the holder unit 250 and the see-through body unit 210 may be maintained.

Meanwhile, in the first embodiment of the present disclosure, although the catching step part 251a and the sliding coupling part 251b are illustrated and described as being integrally formed in the holder extension part 251 of the holder unit 250, in some cases, the catching step part and the sliding coupling part may be separately provided from the holder unit 250.

For example, a coupling member (not illustrated) disposed to surround the outer circumference of the holder extension part 251 may be further provided. Here, the coupling member (not illustrated) may be provided in a ring shape or C-shape and may be made of a synthetic resin material such as a LDPE material. Also, one side of the outer circumference of the holder extension part 251 may be formed to be recessed in the circumferential direction so that the coupling member (not illustrated) is inserted thereinto. At this time, the catching step part and the sliding coupling part may be formed on the outer circumference of the coupling member (not illustrated). Accordingly, as the coupling member (not illustrated) is coupled to the holder extension part 251, the holder unit 250 may be coupled to the inner circumference of the see-through body unit 210.

Meanwhile, the dental implant packaging container 300 may further include a bushing part 252 that includes a ring-shaped body provided to be forcibly fitted into a fitting step part 251c formed on the inner circumference of the lower end portion of the holder unit 250, and bushing support parts 252a provided to integrally protrude downward from an inner side end of the ring-shaped body at UV transmission gaps formed at a plurality of sites in the circumferential direction so as to support the upper end portion of the fixture f and allow the UV light for surface modification to pass through.

Also, the fitting step part 251c that expands to be stepped outward in the radial direction may be formed on the inner circumference of the lower end portion of the holder extension part 251. Here, the fitting step part 251c may be formed to have an inner diameter that corresponds to an outer diameter of the ring-shaped body. Accordingly, as the bushing part 252 is forcibly fitted into the fitting step part 251c, the bushing part 252 may be coupled to the holder unit 250. At this time, in some cases, an adhesive may be applied between the fitting step part 251c and the ring-shaped body to mediate coupling therebetween.

Also, the bushing part 252 may support the upper end portion of the fixture f and may be made of a metal material, such as titanium, which has high strength, excellent corrosion resistance, and biocompatibility so that contamination is prevented when contact occurs between the bushing part 252 and the upper end of the fixture f. Here, although the holder unit 250 and the bushing part 252 are illustrated and described as being separately provided from each other, when the holder unit 250 is made of a metal material such as titanium, the holder unit 250 and the bushing part 252 may be integrally provided.

Also, the bushing support parts 252a may be provided to integrally protrude downward from the inner side end of the ring-shaped body at UV transmission gaps formed at the plurality of sites in the circumferential direction. Here, a vertical length of the bushing support part 252a may be formed as a predetermined minimum support length so that the fixture f is supported by the bushing support part 252a and a surface modification area due to irradiating the fixture f with UV light is maximized. At this time, in a state in which the first cap unit 220, the holder unit 250, and the bushing part 252 are coupled to each other, the vertical lengths of the bushing support parts 252a may be set so that the lower end portions of the bushing support parts 252a are disposed above the lower end portion of the protruding part 222. Accordingly, since the bushing support parts 252a are provided to have the minimum support length in the vertical direction so that the upper end portion of the fixture f is supported thereby and the area in which the fixture f is exposed to UV light irradiated from the outside is maximized, storage stability and surface modification capability may be improved.

Also, the inner diameter of the ring-shaped body and the inner diameter of the bushing support part 252a, which protrudes downward from the inner side end of the ring-shaped body, may be provided to have a size that exceeds the outer diameter of the upper end portion of the fixture f but substantially corresponds thereto. That is, the bushing support part 252a and the fixture f may be disposed to be spaced apart at a predetermined fine interval.

Accordingly, in the state in which the holder unit 250 and the second cap unit 230 are coupled to the see-through body unit 210, the fixture f may be inserted through the hollow of the holder unit 250 and disposed in the accommodation space 214. At this time, the lower end portion of the fixture f may be seated on a base part 231 which will be described below, and the upper end portion of the fixture f may be supported by the bushing support part 252a. Therefore, since the fixture f is stored in the accommodation space 214 and is prevented from coming in contact with the inner circumferential surface 213 of the see-through body unit 210 due to falling, contamination of the fixture f may be prevented. Further, since the bushing support part 252a and the fixture f are disposed to be spaced apart at a predetermined fine interval instead of being brought into close contact, UV light reflected from a metal such as titanium may be irradiated through the interval.

Also, since UV transmission gaps are formed at the plurality of sites in the circumferential direction at the bushing support parts 252a for supporting the upper end portion of the fixture f, a region in which the upper end portion of the fixture f is hidden from the UV light is minimized. In this way, since the area in which the upper end portion of the fixture f is irradiated with the UV light is increased, the surface modification effect may be significantly improved.

Meanwhile, the second cap unit 230 may include a second fixing part 232 fitted and coupled to the lower end portion of the see-through body unit 210 and the base part 231 provided at an inner side end of the second fixing part 232 so that the lower end portion of the fixture f is seated thereon.

Here, the second cap unit 230 may be provided in a cylindrical shape or the like to correspond to the shape of the see-through body unit 210, and a hollow 230b may be formed to vertically pass through a radially inner central portion of the second cap unit 230.

Also, a plurality of second recessed groove portions 234 may be formed to be recessed at predetermined intervals along the circumferential direction in a lower end portion of the second cap unit 230. Accordingly, since the second recessed groove portions 234 are formed to be recessed at predetermined intervals along the circumferential direction in the lower end portion of the second cap unit 230, the dental implant packaging container 300 may be supported and fixed in an upright state in an external fixing device or the like. Therefore, convenience of use may be improved.

Also, the second cap unit 230 may be made of materials such as a synthetic resin. In order to allow UV light for surface modification of the fixture f to pass through the second cap unit 230, the second cap unit 230 may be made of a synthetic resin material such as a transparent or semi-transparent polycarbonate material.

Also, a second support step 232c that comes in contact with the other side end of the see-through body unit 210 may be formed on an outer side of an upper end portion of the second cap unit 230. That is, the second support step 232c may come in contact with the second edge 211b of the see-through body unit 210.

At this time, in the second cap unit 230, the second fixing part 232 may be integrally formed with the second support step 232c in a radially inward direction of the second support step 232c. That is, the second fixing part 232 may be formed to integrally extend and protrude upward from an inner side end of a second cap body 230a of the second cap unit 230.

Specifically, the second fixing part 232 may be integrally formed at the upper end portion of the second cap unit 230. Here, the second fixing part 232 may extend and protrude upward from the upper inner side end of the second cap unit 230 so as to be inserted into the see-through body unit 210.

Accordingly, the second fixing part 232 may be inserted into the other side end of the see-through body unit 210. At this time, since both side ends of the see-through body unit 210 are provided to have the same shape, even when the upper and lower sides of the see-through body unit 210 are switched, the first fixing part 221 and the second fixing part 232 may be inserted into the accommodation space 214 of the see-through body unit 210.

Also, one or more coupling groove portions 232*a* may be formed to be recessed radially inward along the circumferential direction in one side of the outer circumference of the second fixing part 232. At this time, the coupling groove portions 232*a* may be formed to be recessed at a plurality of sites in the vertical direction.

Here, one or more rubber rings 233, which are made of a ring-shaped rubber material or the like, may be provided between the coupling groove portion 232*a* and the inner circumferential surface of the see-through body unit 210. At this time, the rubber ring 233 may be inserted into and fixed to the coupling groove portion 232*a*, which is formed to be recessed radially inward along the circumferential direction in the one side of the outer circumference of the second fixing part 232. Accordingly, during insertion of the second fixing part 232, in which the rubber ring 233 is disposed in the coupling groove portion 232*a*, into the inner circumferential surface of the see-through body unit 210, the second fixing part 232 may be forcibly fitted into and coupled thereto.

Also, in a lower central side of the second fixing part 232, a second recessed portion 230*c* may be formed to be recessed upward and communicate with the hollow 230*b*.

Meanwhile, in the second cap unit 230, second through-passages 232*d*, 232*e*, 232*f*, and 232*g* may be radially disposed in the circumferential direction and formed to be hollow in the longitudinal direction thereof. At this time, although the second through-passages are illustrated and described as being formed at four sites in the first embodiment of the present disclosure, the present disclosure is not limited thereto.

Specifically, inner side ends of the second through-passages 232*d*, 232*e*, 232*f*, and 232*g* may be arranged to surround the second fixing part 232 in the circumferential direction and may communicate therewith. At this time, each of the second through-passages 232*d*, 232*e*, 232*f*, and 232*g* may communicate with the hollow 230*b*. Also, cross-sections of the second through-passages 232*d*, 232*e*, 232*f*, and 232*g* may be formed to have various sizes and shapes, such as a circular shape and a quadrilateral shape, and the sizes of the passages may be uniform.

Here, the first through-passages 222*a* and 222*b* and the second through-passages 232*d*, 232*e*, 232*f*, and 232*g* may be formed in the longitudinal direction in the first cap unit 220 and the second cap unit 230, respectively. Accordingly, the supply of oxygen for ozone generation for surface modification of the fixture f interposed between the first fixing part 221 and the second fixing part 232 may be concentrated. Therefore, since UV light is irradiated and oxygen may be supplied in the amount required for the surface modification process into the accommodation space 214 and may be converted to ozone, the residual amount of ozone may be significantly increased. In this way, since the amount of ozone generated due to UV light for modifying the surface of the fixture f is increased and the effect of surface modification using the UV light is improved, the stability of osseointegration may be improved.

Of course, in some cases, when the first cap unit 220 and the second cap unit 230 are provided to block an air flow between the see-through body unit 210 and the outside, each of the through-passages may not be provided so that the communication of the first cap unit 220 and the second cap unit 230 in the vertical direction is blocked. In this way, the surface modification of the fixture f may be performed as UV irradiation occurs when only oxygen is inside the see-through body unit 210 whose communication with outside air is blocked. Also, in some cases, the shape of the first through-passage formed in the first cap unit 220 may be the same as the shape of the second through-passages 232*d*, 232*e*, 232*f*, and 232*g* formed in the second cap unit 230.

Meanwhile, the base part 231 may be provided on the upper end portion of the second fixing part 232 so that the lower end portion of the fixture f is seated thereon. Here, the base part 231 may be provided to be integrally formed with the second cap unit 230 or may be separately provided from the second cap unit 230 and disposed on the upper end portion of the second fixing part 232.

Specifically, on an edge of an upper surface of the base part 231, guide parts 231*c* may be provided to radially protrude at UV transmission gaps at a plurality of sites in the circumferential direction, and a corner portion 231*e* that comes in point contact with an end portion of the fixture f may be formed on an inner side end of the guide part 231*c*. Also, a seating groove 231*b* on which the lower end portion of the fixture f is seated may be formed on a bottom surface of the inner side of the base part 231 that is surrounded by the guide parts 231*c*.

Also, a fitting part 231*a* may be formed to extend and protrude downward from the lower portion of the base part 231. Here, a fitting groove 232*b* may be formed to be recessed in the upper end portion of the second fixing part 232 so that the fitting part 231*a*, which extends and protrudes downward from the lower portion of the base part 231, is fitted into and coupled to the fitting groove 232*b* and fixed. Therefore, as the fitting part 231*a* is forcibly fitted into and fixed to the fitting groove 232*b*, the base part 231 may be fixed to the second fixing part 232. In this way, when the second cap unit 230 is coupled to the see-through body unit 210, the lower end portion of the fixture f may be seated and disposed on the upper surface of the base part 231 and supported.

Also, there is a concern that, when the fixture f is irradiated with UV light to perform surface modification, a portion of the fixture f that is supported by the base part 231 may be blocked, making it impossible to perform surface modification on the corresponding portion. Specifically, the lower end portion of the fixture f may be inserted into a gum of the human body in the process of implant surgery. Accordingly, there is a concern that, when the hydrophilicity of the lower end portion of the fixture f is degraded, the osseointegration period may be increased and the recovery period until the implant is stabilized may be increased.

Therefore, the plurality of guide parts 231*c* may be provided to radially protrude at UV transmission gaps on the edge of the upper surface of the base part 231. Here, the guide parts 231*c* may be provided to extend and protrude from the outer side of the upper surface of the base part 231, and the sizes of the guide parts 231*c* may be substantially the same.

Accordingly, since the UV transmission gaps are formed at the plurality of sites along the circumferential direction on the edge of the upper surface of the base part 231 for supporting the lower end portion of the fixture f, a region in which the fixture f is hidden from the UV light is minimized. In this way, since the area in which the lower end portion of the fixture f is irradiated with the UV light is increased, the surface modification effect may be significantly improved.

Further, an inclined surface 231d may be formed on an inner side end of the guide part 231c. Accordingly, on one side of the inclined surface 231d, the corner portion 231e may be formed to come in point contact with the outer circumference of the fixture f and support the fixture f and to minimize the portion of the fixture f hidden from the UV light.

Here, when UV light is irradiated, since the UV light passes through a space in which the UV transmission gaps are formed and reaches the fixture f, the portion of the fixture f hidden by the guide part 231c may be minimized. Further, since the corner portion 231e is formed, an area in which the fixture f comes in contact with the UV light may be maximized. Accordingly, surface modification may be smoothly performed on a lower end portion of an abutment a.

Meanwhile, the fixture f is inserted into or withdrawn from the accommodation space 214 using surgical tools such as tweezers or a drilling device. Also, an operator fastens a surgical tool to the inner circumferential fastening groove f in the upper end portion of the fixture f in order to insert or withdraw the fixture f. At this time, a fastening part of the surgical tool may be forcibly fitted into and coupled to the inner circumferential fastening groove h of the fixture f. In the fastening process, the operator presses the fixture f in the process in which the fastening part of the surgical tool is forcibly fitted into the inner circumferential fastening groove h of the fixture f so as to be fastened thereto.

Here, when the fixture f falls into the accommodation space 214, the surface of the fixture f may be contaminated due to bacteria, or foreign matter may adhere to the surface of the fixture f. At this time, the operator may perform the first surface modification treatment and the first sterilization treatment on the fixture f again to prevent infection of a subject of fixture f placement surgery. Further, since it is inconvenient and takes some time for the operator to perform the entire process, including the first sterilization treatment, the second surface modification treatment, and the like, again, there is a concern that work efficiency may be degraded.

Here, the corner portion 231e may come in contact with the outer circumference of the fixture f and support the lower end portion of the fixture f. Also, the seating groove 231b on which the lower end portion of the fixture f is seated may be formed in the center of the upper surface of the base part 231. Accordingly, in the guide part 231c, the corner portion 231e, which comes in point contact with the circumference of the fixture f and supports the fixture f, and the seating groove 231b, on which the lower end portion of the fixture f is seated, may be formed. Therefore, since the guide part 231c supports the fixture f and prevents the fixture f from falling into the accommodation space when the fixture f is pressed to be withdrawn, the storage stability of the device may be further improved.

Also, the base part 231 may be made of a metal material, such as titanium, which has high strength, excellent corrosion resistance, and biocompatibility. At this time, since the base part 231 is made of the material such as titanium, the UV light reflected from the titanium surface may be transmitted to the fixture f, and surface modification capability may be improved. Therefore, since the portion of the fixture f covered from the UV light due to the base part 231 is minimized while the fixture f is seated on the base part 231 and supported, surface modification capability may be significantly increased.

Here, although the base part 231 is illustrated and described as being forcibly fitted into and fixed to the fitting groove 232b of the second fixing part 232 in the present embodiment, the base part 231 and the second fixing part 232 may also be integrally provided.

Figure 8:
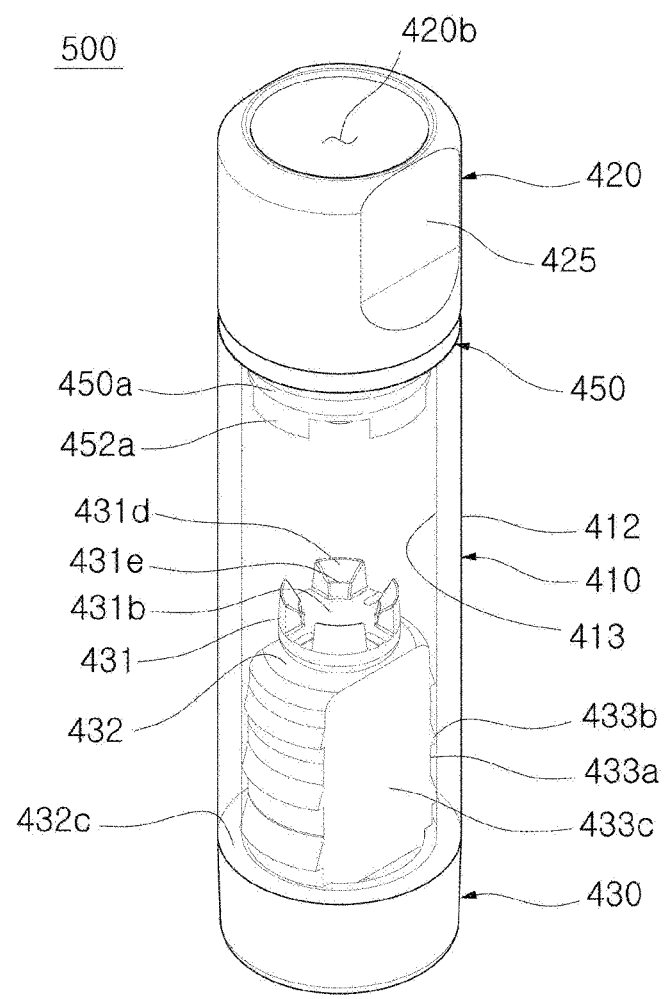
FIG. 8 is a perspective view of a dental implant packaging container according to a second embodiment of the present disclosure in which the inside of the dental implant packaging container is visible.
Figure 9:
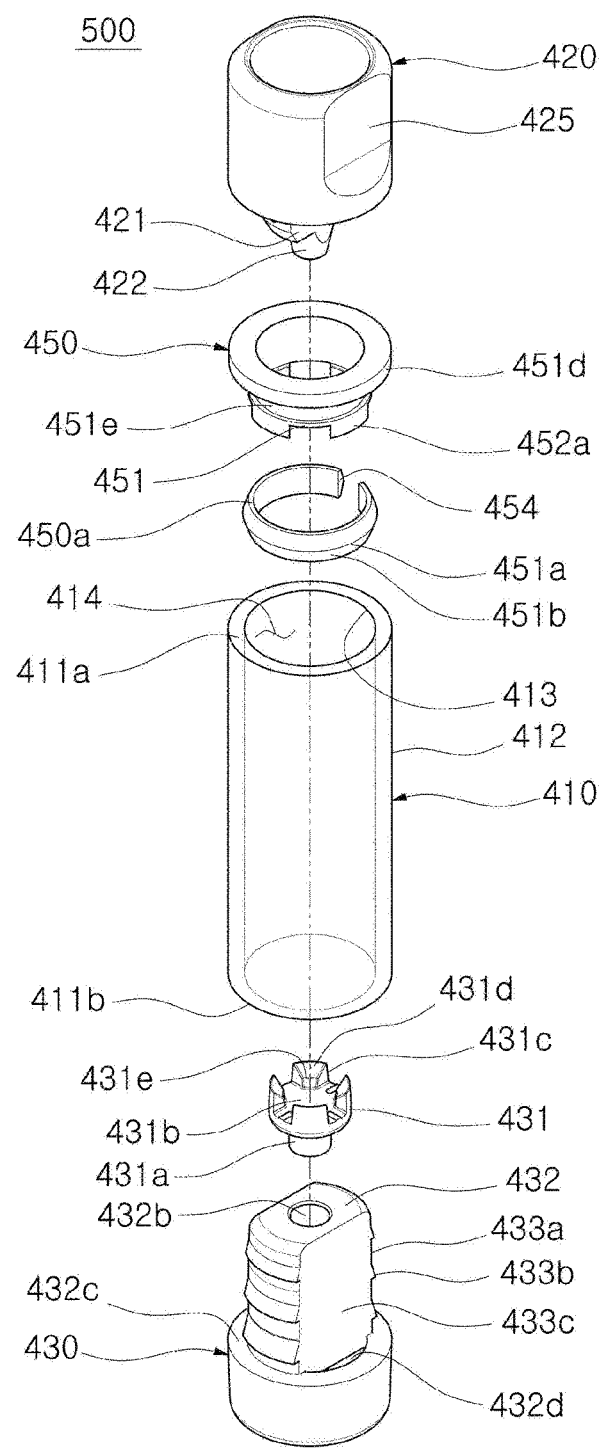
FIG. 9 is an exploded perspective view of the dental implant packaging container according to the second embodiment of the present disclosure.
Figure 10:
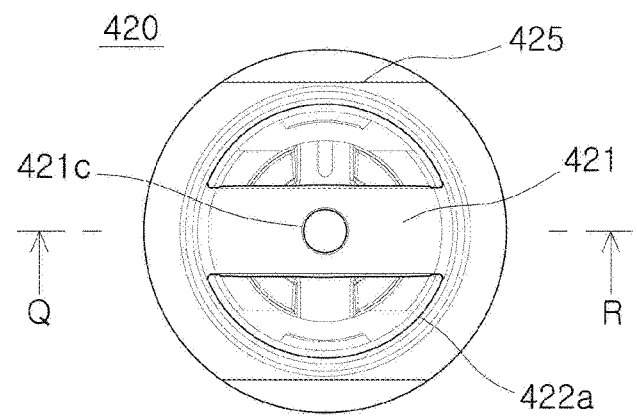
FIG. 10 is a top view of the dental implant packaging container according to the second embodiment of the present disclosure.
Figure 11A:
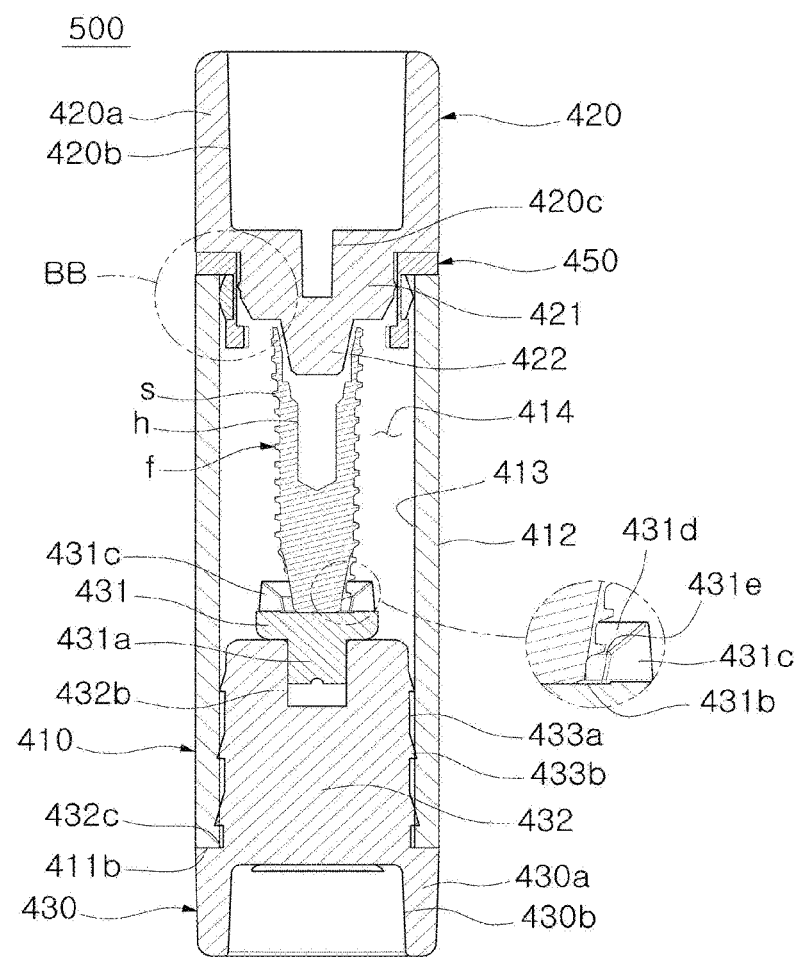
FIG. 11A is a cross-sectional view taken along line Q-R of FIG. 10.
Figure 11B:
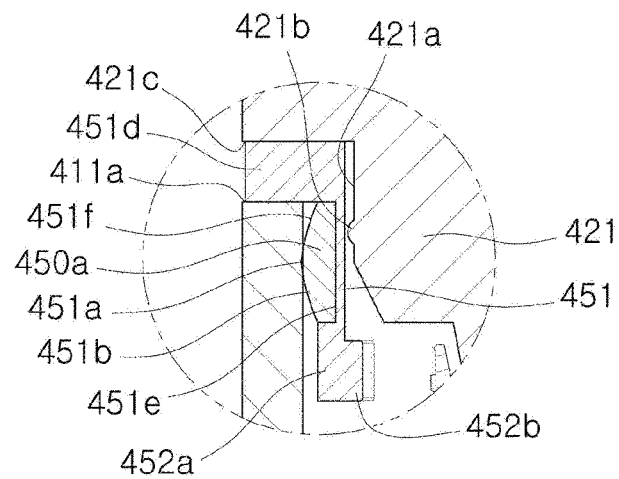
FIG. 11B is an enlarged view of portion BB of FIG. 11A.
Figure 12:
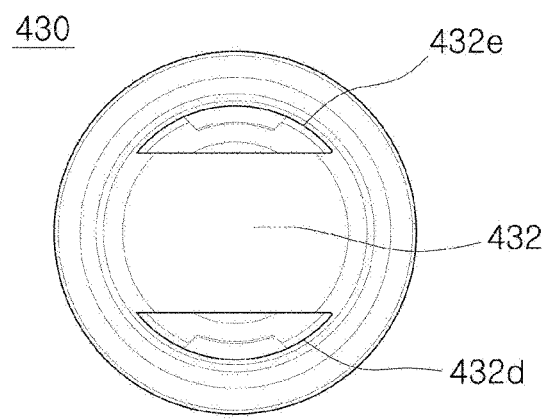
FIG. 12 is a bottom view of the dental implant packaging container according to the second embodiment of the present disclosure.
Figure 13:
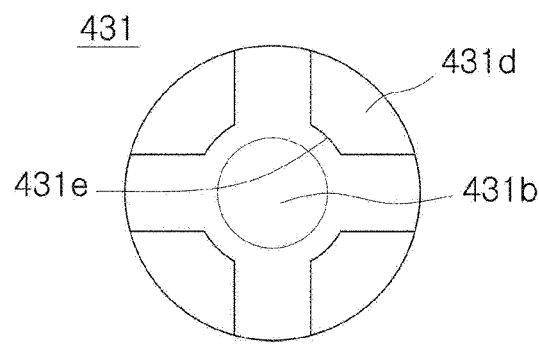
FIG. 13 is a top view illustrating a base part of the dental implant packaging container according to the second embodiment of the present disclosure.
Figure 14:
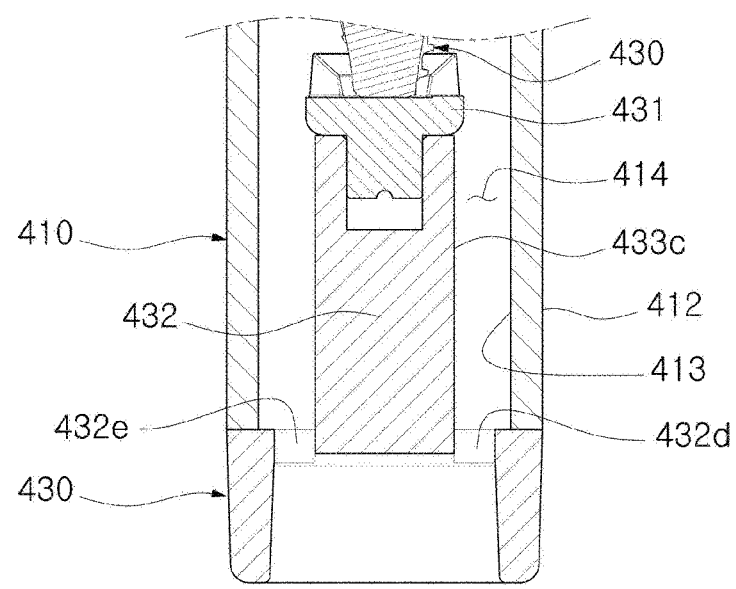
FIG. 14 is a partial cross-sectional view of a lower portion of the dental implant packaging container according to the second embodiment of the present disclosure as viewed from another angle.

Meanwhile, FIG. 8 is a perspective view of a dental implant packaging container according to a second embodiment of the present disclosure in which the inside of the dental implant packaging container is visible, and FIG. 9 is an exploded perspective view of the dental implant packaging container according to the second embodiment of the present disclosure. Also, FIG. 10 is a top view of the dental implant packaging container according to the second embodiment of the present disclosure, and FIG. 11A is a cross-sectional view taken along line Q-R of FIG. 10. Also, FIG. 11B is an enlarged view of portion BB of FIG. 11A, and FIG. 12 is a bottom view of the dental implant packaging container according to the second embodiment of the present disclosure. Also, FIG. 13 is a top view illustrating a base part of the dental implant packaging container according to the second embodiment of the present disclosure, and FIG. 14 is a partial cross-sectional view of a lower portion of the dental implant packaging container according to the second embodiment of the present disclosure as viewed from another angle. In the present embodiment, since basic configurations are the same as in the first embodiment except for a second cap unit 430 and a holder unit 450, detailed description of the same configurations will be omitted.

As illustrated in FIGS. 8 to 14, a dental implant packaging container 500 according to the second embodiment of the present disclosure includes a see-through body unit 410, a first cap unit 420, the second cap unit 430, and the holder unit 450.

Meanwhile, the second cap unit 430 may include a hollow second cap body 430a disposed on a lower end of the see-through body unit 410, and a second fixing part 432 which is formed to protrude from an upper portion of the second cap body 430a so as to be fitted and coupled to a lower end portion of the see-through body unit 410 and which has a fitting surface 433a formed on an outer side portion thereof.

Also, the second fixing part 432 may be formed in the shape of a bar crossing a hollow 430b of the second cap body 430a and protrude upward, and a separation space may be formed between an outer side of a cutting surface 433c, which is formed at a side surface of the second fixing part 432, and an inner circumference of the see-through body unit 410.

Here, a length of the bar of the second fixing part 432 in the longitudinal direction thereof may be formed to substantially correspond to an inner diameter of the see-through body unit 410. At this time, an outer surface profile of the fitting surface 433a may be formed to be round so as to correspond to the profile of the inner circumference of the see-through body unit 410.

Accordingly, the fitting surface 433a on the outer side portion of the second fixing part 432, which is formed in the shape of a bar that crosses the hollow 430b of the second cap body 430a, may be detachably fitted and coupled to an inner circumferential surface of the see-through body unit 410.

Here, on the fitting surface 433a, a plurality of fitting protrusions 433b, each having an upper surface portion formed to protrude to be inclined inward in the radial direction toward the upper side and a lower surface portion formed to be stepped, may be provided at predetermined intervals in the vertical direction. Specifically, each of the fitting protrusions 433b may be formed so that a lower portion protrudes to be stepped outward in the radial direction and is inclined inward in the radial direction toward the upper side. At this time, "protruding to be stepped" may be understood as meaning that a boundary portion between an outer surface of the fitting surface 433a, on which the fitting protrusion 433b is not formed, and a lower portion of the fitting protrusion 433b is formed to be bent.

Accordingly, during insertion of the second fixing part 432, in which the plurality of fitting protrusions 433b are formed on the fitting surface 433a, into the inner circumferential surface of the see-through body unit 410, the second fixing part 432 may be forcibly fitted and coupled thereto.

Therefore, the plurality of fitting protrusions 433b may be formed on the fitting surface 433a on the outer side portion of the second fixing part 432, which is formed to cross the hollow 430b in the inner circumference of the second cap unit 430, and may be simultaneously fitted and coupled to the inner circumferential surface of the see-through body unit 410. In this way, since the fixture f may be safely stored, convenience of use and safety may be improved.

Meanwhile, in the second cap unit 430, semi-circular second through-passages 432d and 432e may be formed at a plurality of sites so as to surround the second fixing part 432. Here, the second through-passages 432d and 432e may communicate with the separation space and an accommodation space 414 to allow the supply of oxygen that is converted to ozone to modify the surface of the fixture f.

Specifically, an inner side end of each of the second through-passages 432d and 432e may be arranged to surround the second fixing part 432 in the circumferential direction and communicate therewith. At this time, each of the second through-passages 432d and 432e may communicate with the hollow 430b.

Also, cross-sections of the second through-passages 432d and 432e may be formed to be semi-circular between the inner circumferential surface of the second cap body 430a and the second fixing part 432. Also, the sizes of the second through-passages 432d and 432e may be uniform.

In this way, the semi-circular second through-passages 432d and 432e may be formed to communicate with the separation space, which is formed between the cutting surface 433c and the inner circumference of the see-through body unit 410, and to surround the second fixing part 432. Therefore, since the amount of oxygen flowing in from the outside to modify the surface of the fixture f is increased, surface modification performance may be improved. That is, since the separation space communicates with the outside and the accommodation space 414, the flow of oxygen for ozone generation is sufficiently formed on the fixture f which is subject to surface modification, and thus the surface modification performance may be improved.

Accordingly, the areas of the second through-passages 432d and 432e, except for the areas thereof covered by the bar-shaped second fixing part 432, may communicate with the hollow 430b. Therefore, since the areas of the second through-passages 432d and 432e are maximized and the amount of oxygen flowing in from the outside increases, the surface modification performance may be improved. Further, since the sizes of the second through-passages 432d and 432e are formed to be uniform and oxygen flowing into the see-through body unit 410 is uniformly distributed thereto, homogeneity may be secured during the surface modification of the fixture f.

Of course, in some cases, when the first cap unit 420 and the second cap unit 430 are provided to block an air flow between the see-through body unit 410 and the outside, each of the through-passages may not be provided so that the communication of the first cap unit 420 and the second cap unit 430 in the vertical direction is blocked. In this way, the surface modification of the fixture f may be performed as UV irradiation occurs when only oxygen is inside the see-through body unit 410 whose communication with outside air is blocked. Also, in some cases, the shape of the first through-passage formed in the first cap unit 420 may be the same as the shape of the second through-passages 432d and 432e formed in the second cap unit 430.

Meanwhile, the holder unit 450 may be provided to mediate the connection between the see-through body unit 410 and the first cap unit 420 by having an outer circumferential portion coupled to the inner circumference of the see-through body unit 410 and an inner circumferential portion coupled to a coupling surface 421a. Also, bushing support parts 452a may be provided to integrally protrude downward from an end portion of a holder extension part 451 at UV transmission gaps at a plurality of sites in the circumferential direction so as to support the upper end portion of the fixture f and allow the UV light for surface modification to pass through.

Also, the bushing support parts 452a may be provided to integrally protrude downward from the inner side end of the ring-shaped body at UV transmission gaps formed at the plurality of sites in the circumferential direction. Here, a vertical length of the bushing support part 452a may be formed as a predetermined minimum support length so that the fixture f is supported by the bushing support part 452a and a surface modification area due to irradiating the fixture f with UV light is maximized. At this time, in a state in which the first cap unit 420 and the holder unit 450 are coupled to each other, the vertical lengths of the bushing support parts 452a may be set so that the lower end portions of the bushing support parts 452a are disposed above the lower end portion of a protruding part 422.

Accordingly, since the bushing support parts 452a are provided so that the upper end portion of the fixture f is supported thereby and the area in which the fixture f is exposed to UV light irradiated from the outside is maximized, storage stability and surface modification performance may be improved.

Also, on an end portion of the bushing support part 452a, a support protrusion 452b may be formed to extend and protrude inward in the radial direction so as to support an end portion of the fixture f. At this time, an inner diameter connecting the inner side ends of the support protrusions 452b may be formed to exceed an outer diameter of the upper end portion of the fixture f.

Here, the support protrusion 452b may be provided so that a width thereof in the circumferential direction narrows in a radially inward direction. Accordingly, since the width of the support protrusion 452b narrows in the radially inward direction, the upper end portion of the fixture f may be irradiated with the UV light for surface modification through the UV transmission gaps.

Also, a support recessed groove may be formed to be recessed in an inner side end of the support protrusion 452b so that the fixture f is caught and supported in the support recessed groove. At this time, the fixture f may be inserted and withdrawn between the end portions of the inner side ends of the support protrusions 452b in which the support recessed grooves are formed. Also, the upper end portion of the fixture f inserted into the dental implant packaging container 500 may come in contact with and may be supported by the support recessed grooves.

Accordingly, since the upper end portion of the fixture f is supported by the support protrusions 452b protruding inward in the radial direction and the fixture f is prevented from falling into the accommodation space 414, stability may be further improved. Of course, in some cases, the bushing support part 452a and the fixture f may be disposed to be spaced apart at a predetermined fine interval without the support protrusion 452b formed therebetween.

In this way, in the state in which the holder unit 450 and the second cap unit 430 are coupled to the see-through body unit 410, the fixture f may be inserted through the hollow of the holder unit 450 and disposed in the accommodation space 414. At this time, the lower end portion of the fixture f may be seated on a base part 431 which will be described below, and the upper end portion of the fixture f may be supported by the bushing support part 452a and the support protrusion 452b. Therefore, since the fixture f is stored in the accommodation space 414 and is prevented from coming in contact with an inner circumferential surface 413 of the see-through body unit 410 due to falling, contamination of the fixture f may be prevented. Further, since the bushing support part 452a and the fixture f are disposed to be spaced apart at a predetermined fine interval instead of being brought into close contact, UV light reflected from a metal such as titanium may be irradiated through the interval.

Also, since UV transmission gaps are formed at the plurality of sites along the circumferential direction in the bushing support parts 452a for supporting the upper end portion of the fixture f, a region in which the upper end portion of the fixture f is hidden from the UV light is minimized. In this way, since the area in which the upper end portion of the fixture f is irradiated with the UV light is increased, the surface modification effect may be significantly improved.

Also, the holder extension part 451 may protrude downward to be inserted into the inner circumference of the see-through body unit 410 from the inner side end of a hollow body 451d, and a recessed groove 451e may be formed to be recessed in an outer surface of the holder extension part 451 in the circumferential direction.

Meanwhile, the holder unit 450 may further include a ring part 450a that is provided in a ring shape, surrounds the holder extension part 451, and is disposed to be inserted into the recessed groove 451e. Also, the ring part 450a may have an outer surface formed to protrude outward in the radial direction and may be inclined inward in the radial direction toward the upper and lower sides so that, when the ring part 450a is coupled to the inner circumference of the see-through body unit 410, a frictional fixing force is increased in the withdrawal direction. Here, in an outer circumferential portion of the ring part 450a, a central side in the vertical direction may expand and protrude outward in the radial direction along the circumferential direction and may be formed to be inclined inward in the radial direction toward the upper and lower sides. Of course, in some cases, the ring part 450a may have an outer surface formed to protrude to be stepped outward in the radial direction and formed to be inclined inward in the radial direction toward the lower side.

Specifically, on the outer circumference of the ring part 450a, an expansion part 451a may be formed to expand and protrude outward in the radial direction so that the frictional fixing force is increased in the withdrawal direction with respect to the see-through body unit 410. Also, sliding coupling parts 451b and 451f may be formed to extend from outer circumferential surfaces at upper and lower sides of the expansion part 451a so as to be inclined inward in the radial direction toward the lower side and fitted and fixed to the inner circumferential surface of the see-through body unit 410.

Here, the withdrawal direction refers to a direction from a lower side to an upper side in the longitudinal direction of the see-through body unit 410 when the holder unit 450 is coupled to the upper end portion of the see-through body unit 410 in the longitudinal direction thereof.

Accordingly, during insertion of the sliding coupling parts 451b and 451f, which have a radius decreasing from the upper side to lower side so that the sliding coupling parts 451b and 451f are inclined inward in the radial direction, into the inner circumference of the see-through body unit 410, the holder extension part 451 with a gradually increasing radius may be fitted and coupled to the inner circumference of the see-through body unit 410. At this time, when the sliding coupling parts 451b and 451f are fitted and coupled to the inner circumference of the see-through body unit 410, the entire end surfaces of the sliding coupling parts 451b and 451f may be substantially brought into close contact with the inner circumferential surface of the see-through body unit 410 due to being fitted and coupled thereto. Also, during withdrawal of the sliding coupling parts 451b and 451f from the see-through body unit 410, since the entire end surfaces of the sliding coupling parts 451b and 451f are substantially brought into close contact with the inner circumferential surface of the see-through body unit 410, the holder unit 450 is not withdrawn from the see-through body unit 410 unless an external force of a predetermined magnitude or more is exerted on the holder unit 450 in the withdrawal direction.

Further, not only the contact area between the holder unit 450 and the see-through body unit 410 is wider than the contact area between the first cap unit 420 and the holder unit 450, but also the sliding coupling parts 451b and 451f may slide to be fitted and coupled to the inner circumference of the see-through body unit 410. Therefore, the coupling force between the holder unit 450 and the see-through body unit 410 may be provided to be larger than the coupling force between the first cap unit 420 and the holder unit 450, which are coupled while the contact area therebetween is minimized.

In this way, even when the first cap unit 420 is separated from the holder unit 450, the state in which the holder unit 450 is coupled to the see-through body unit 410 may be maintained. That is, the holder unit 450 coupled to the inner circumference of the see-through body unit 410 is not separated therefrom due to the external force that is applied when the first cap unit 420, which is fitted and coupled to the inner circumferential portion of the holder unit 450, is separated from the holder unit 450. Therefore, the frictional fixing force between the holder unit 450 and the see-through body unit 410 in the withdrawal direction is increased, and even when the first cap unit 420 is removed, the coupling state between the holder unit 450 and the see-through body unit 410 may be maintained.

Also, the ring part 450a may be made of a synthetic resin material such as a LDPE material. In some cases, the ring part 450a may be made of a metal material, such as titanium, which has high strength, excellent corrosion resistance, and biocompatibility.

Meanwhile, the ring part 450a may have open one side so that the ring part 450a is compatibly applied to an outer diameter of the holder extension part 451. Here, at one side of the ring part 450a, a clearance portion 454 may be formed to be open in the shape of a slit having a predetermined length in the circumferential direction.

Here, even when the ring part 450a is provided to be smaller than the outer diameter of the holder extension part 451, an opening gap at the clearance portion 454 may be expanded so that the ring part 450a may surround the outer circumference of the holder extension part 451.

Accordingly, the ring part 450a, which is fitted and coupled to the inner circumference of the see-through body unit 410 and is disposed to surround the holder extension part 451, may have open one side. In this way, even when the outer diameter of the ring part 450a is provided to have a size different from the outer diameter of the holder extension part 451, the ring part 450a may be compatibly applied to the holder extension part 451. Thus, compatibility may be improved.

Figure 15:
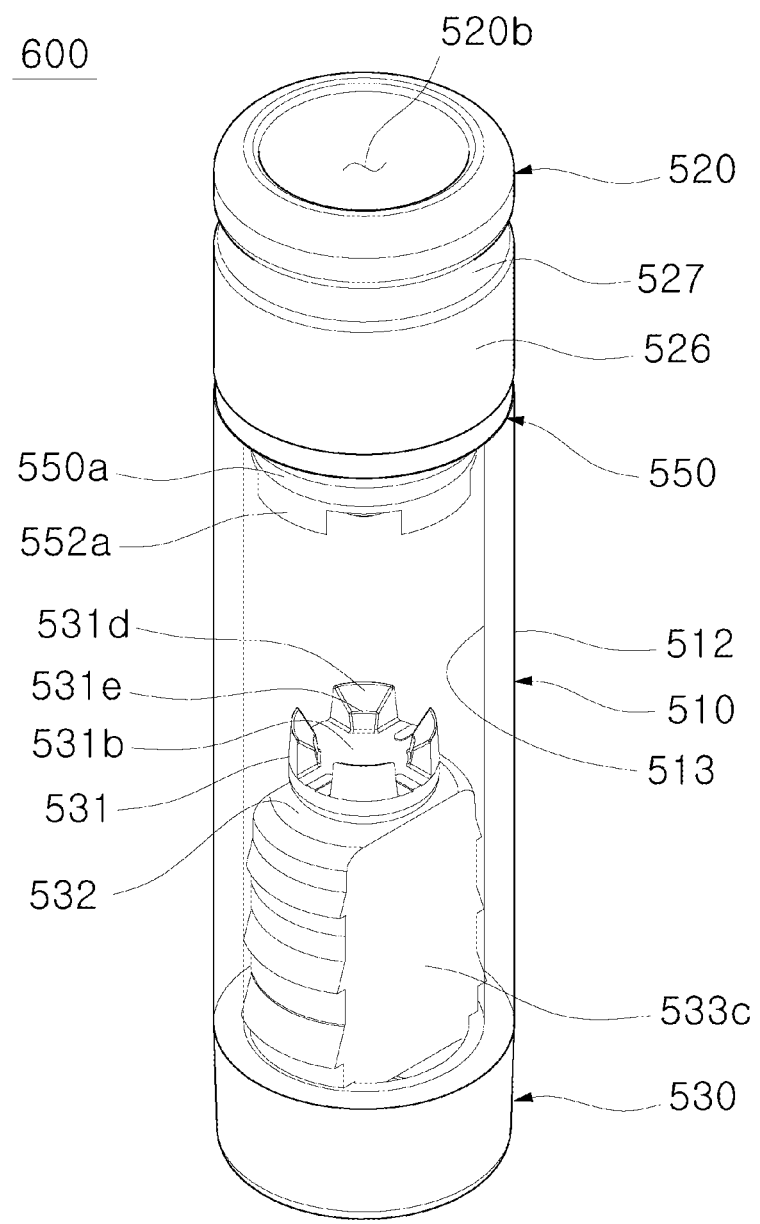
FIG. 15 is a perspective view of a dental implant packaging container according to a third embodiment of the present disclosure in which the inside of the dental implant packaging container is visible.
Figure 16:
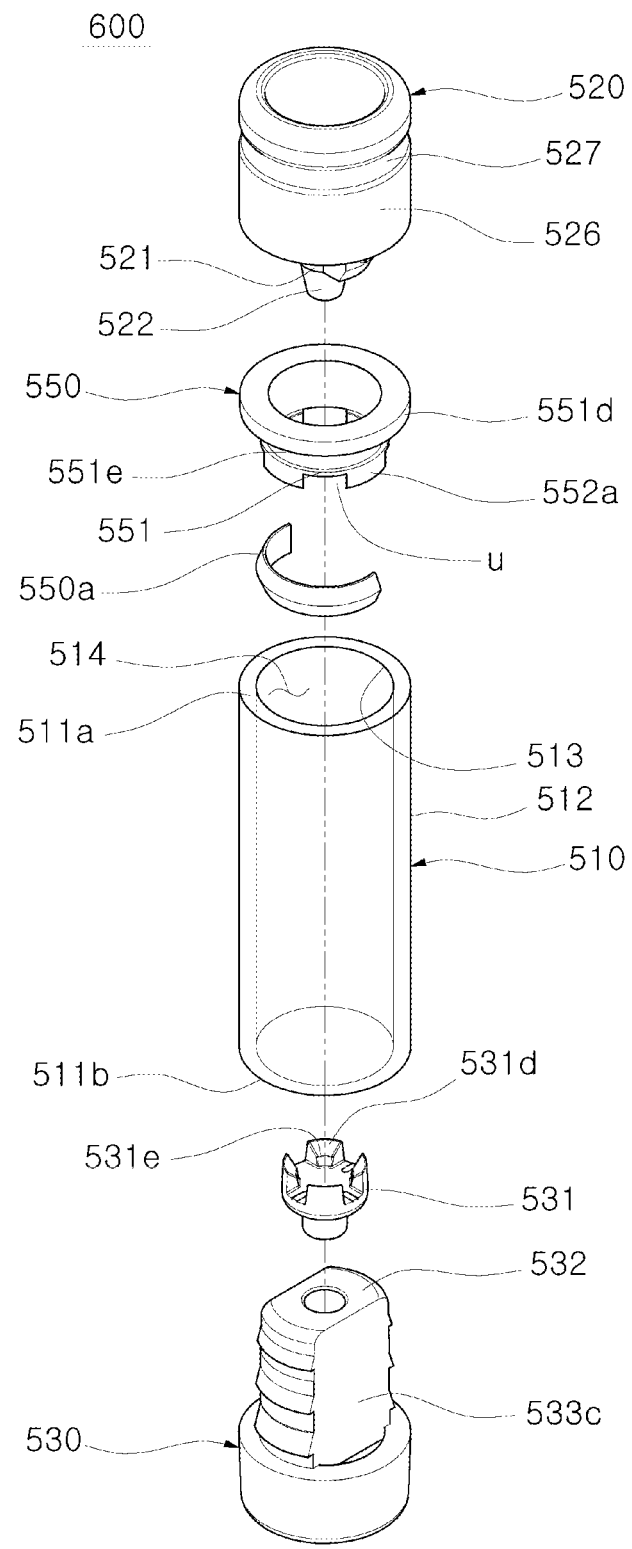
FIG. 16 is an exploded perspective view of the dental implant packaging container according to the third embodiment of the present disclosure.
Figure 17:
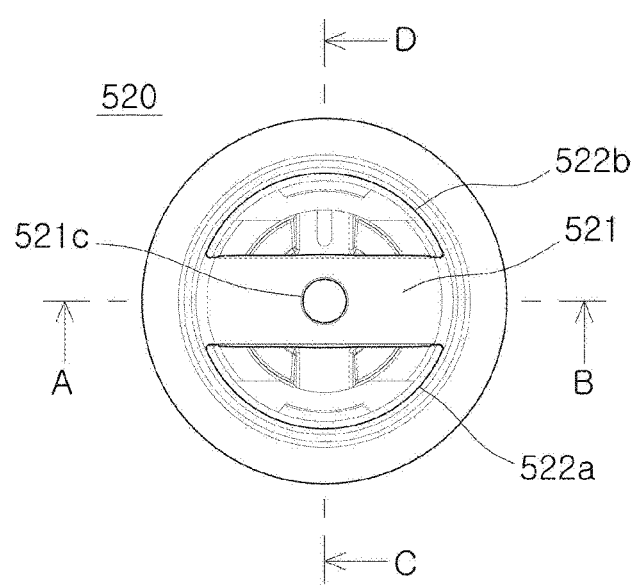
FIG. 17 is a top view of the dental implant packaging container according to the third embodiment of the present disclosure.
Figure 18:
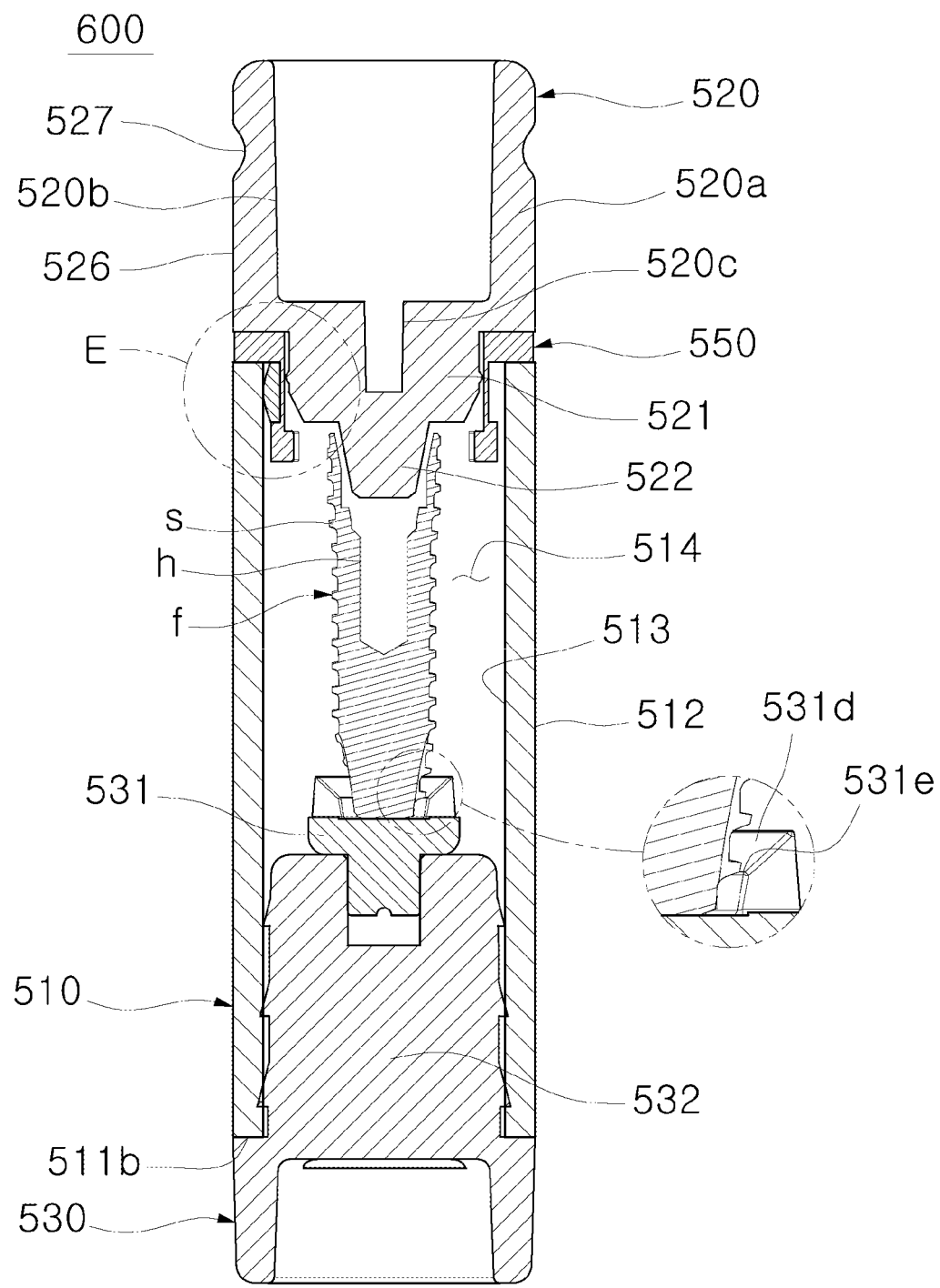
FIG. 18 is a cross-sectional view taken along line A-B of FIG. 17.
Figure 19:
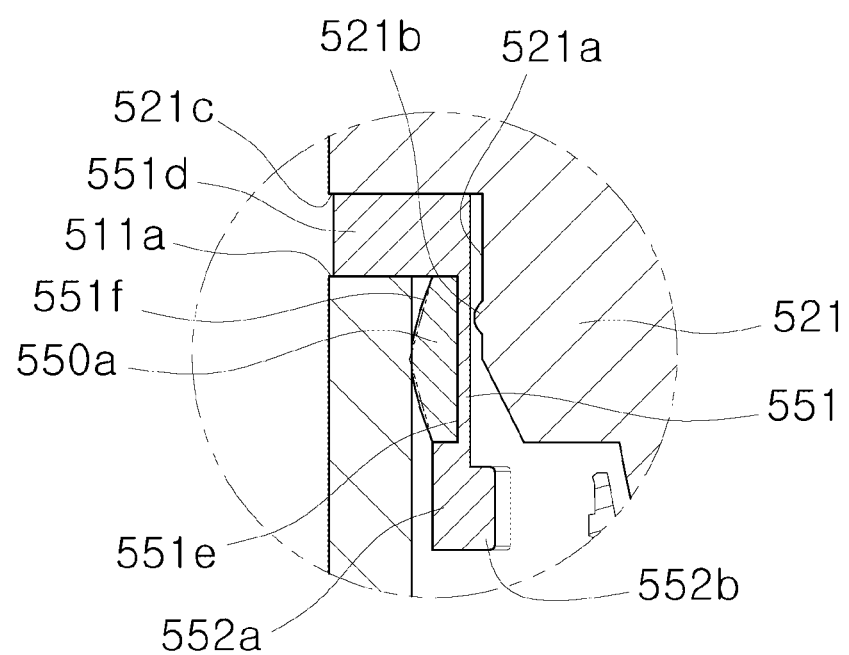
FIG. 19 is an enlarged view of portion E of FIG. 18.
Figure 20:
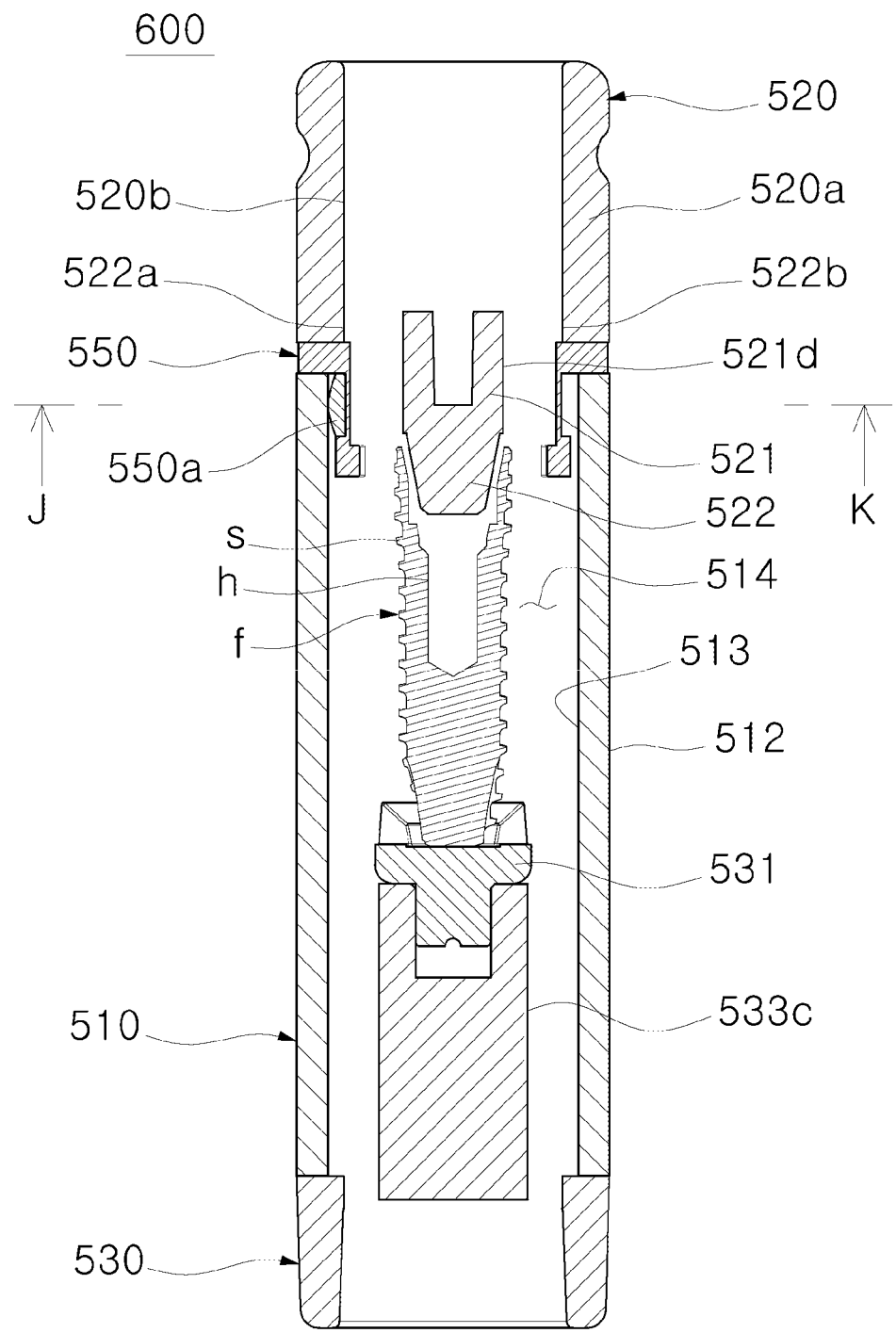
FIG. 20 is a cross-sectional view taken along line C-D of FIG. 17.
Figure 21:
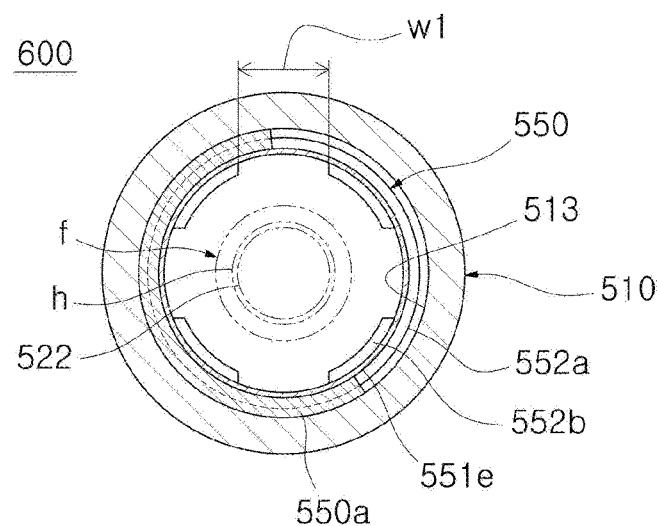
FIG. 21 is a cross-sectional view taken along line J-K of FIG. 20.
Figure 22:
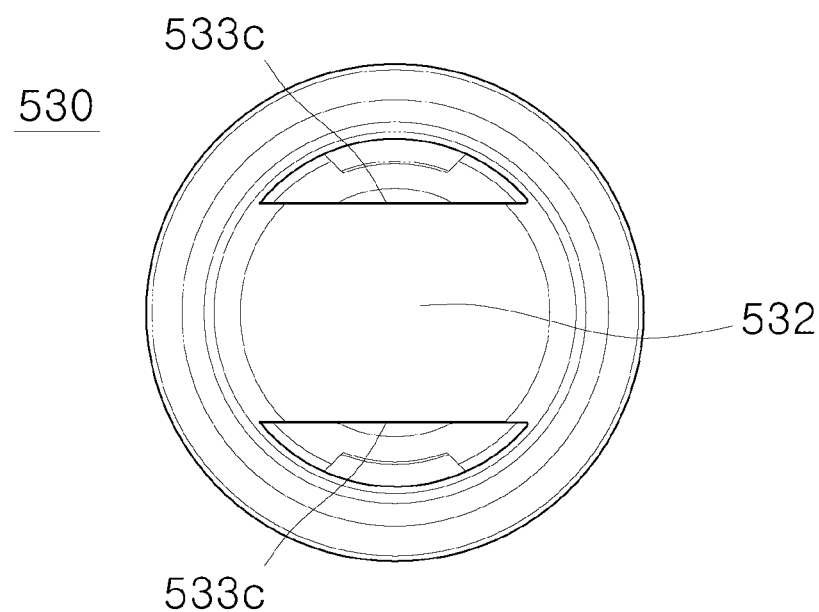
FIG. 22 is a bottom view of the dental implant packaging container according to the third embodiment of the present disclosure.
Figure 23:
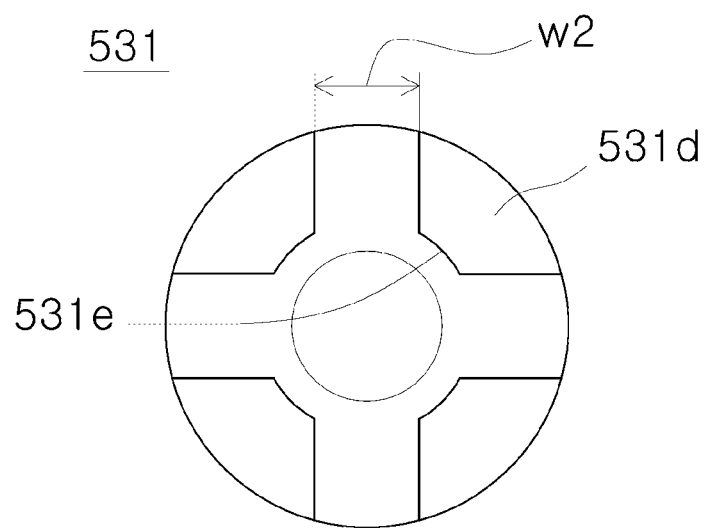
FIG. 23 is a top view illustrating a base part of the dental implant packaging container according to the third embodiment of the present disclosure.

Meanwhile, FIG. 15 is a perspective view of a dental implant packaging container according to a third embodiment of the present disclosure in which the inside of the dental implant packaging container is visible, and FIG. 16 is an exploded perspective view of the dental implant packaging container according to the third embodiment of the present disclosure. Also, FIG. 17 is a top view of the dental implant packaging container according to the third embodiment of the present disclosure, and FIG. 18 is a cross-sectional view taken along line A-B of FIG. 17. Also, FIG. 19 is an enlarged view of portion E of FIG. 18, and FIG. 20 is a cross-sectional view taken along line C-D of FIG. 17. Also, FIG. 21 is a cross-sectional view taken along line J-K of FIG. 20, and FIG. 22 is a bottom view of the dental implant packaging container according to the third embodiment of the present disclosure. Also, FIG. 23 is a top view illustrating a base part of the dental implant packaging container according to the third embodiment of the present disclosure. In the present embodiment, since basic configurations are the same as in the second embodiment except for a first cap unit 520 and a holder unit 550, detailed description of the same configurations will be omitted.

As illustrated in FIGS. 15 to 23, a dental implant packaging container 600 according to the third embodiment of the present disclosure includes a see-through body unit 510, the first cap unit 520, the holder unit 550, and a second cap unit 530.

Meanwhile, the first cap unit 520 may be disposed at one side of the see-through body unit 510, and the first cap unit 520 may include a first cap body 520a, a first fixing part 521, and a protruding part 522.

Specifically, the first cap body 520a may be provided in a cylindrical shape of which a diameter of an outer circumference corresponds to that of an outer circumference 512 of the see-through body unit 510, and a marking part 526 may be provided on an outer circumferential surface of the first cap body 520a. Here, on the marking part 526, information such as specifications and date of manufacture of the fixture f, which is accommodated in an accommodation space 514, are indicated by letters or symbols. The marking part 526 is manufactured as a sticker and then selectively attached according to the specifications of each fixture f. Since an outer circumferential surface of the first cap body 520a is provided to maintain a substantially circular profile, the marking part 526 may be easily attached thereto.

At this time, the marking part 526 may be provided to have a size that corresponds to the entire outer circumferential surface of the first cap body 520a but may also be attached to be biased toward one side or the other side of the first cap body 520a. Also, a grip groove portion 527 may be formed in the circumferential direction of the first cap body 520a that is exposed at one side or the other side of the marking part 526. For example, the grip groove portion 527 is formed in a ring shape, which is recessed radially inward along the circumferential direction, on one side of the outer circumferential surface of the first cap body 520a, and the marking part 526 is attached to be biased toward the other side of the first cap body 520a, that is, attached to the outer circumferential surface at an end portion side from which the first fixing part 521 protrudes.

Here, since the grip groove portion 527 is formed in the circumferential direction of the first cap body 520a, the grip groove portion 527 is formed to be perpendicular to the withdrawal direction in which a pulling force is applied to remove the first cap unit 520. Therefore, when the worker holds and pulls the first cap unit 520 to withdraw the fixture f, the worker's hand or mounting tool may be prevented from sliding. Also, since the grip groove portion 527 is formed to be biased toward one side or the other side of the first cap body 520a instead of being formed on the entire outer circumferential surface of the first cap body 520a, a sufficient area for attaching the marking part 526 may be secured. In this way, shielding of UV light due to attachment of the marking part 526 to the see-through body unit 510 may be prevented, and since the entire outer surface of the fixture f is uniformly irradiated with UV light, surface modification capability and sterilizing and cleaning capability may be significantly improved.

Further, the grip groove portion 527 is formed in a shape that is recessed inward in the radial direction from the outer circumference of the first cap body 520a. Therefore, even when the grip groove portion 527 is formed, the outer circumferences of the first cap unit 520, the see-through body unit 510, and the second cap unit 530 maintain a substantially-continuous cylindrical profile. In this way, even when the fixture f is seated on an upper side of a UV lamp arranged in a transverse direction and a surface of the fixture f is treated as the fixture f is rotated in conjunction with the UV lamp, the rotation occurs while the outer circumference of the UV lamp and the entire outer circumference of the dental implant packaging container 600 substantially come in contact. Therefore, the rotation stably occurs while the shaking of the dental implant packaging container 600 is minimized, and in this way, the outer surface of the fixture f may be uniformly irradiated with UV light.

Also, since the grip groove portion is formed to be biased toward one side on the outer circumference of the first cap unit and prevents sliding during mounting, and an area to which the marking part, on which information of a stored fixture is indicated, may be attached is secured on the other side of the outer circumference of the first cap unit, the entire area of the see-through body unit may be formed as a UV light transmission region, and thus, UV transmittance may be significantly improved.

Meanwhile, the holder unit 550 is provided to mediate the connection between the see-through body unit 510 and the first cap unit 520 and is formed in a hollow shape in which an outer circumferential portion corresponds to an inner circumference 513 at one side of the see-through body unit 510 and an inner circumferential portion is coupled to a coupling surface 521a.

Also, a fitting ring part 550a of which an inner circumference is inserted into a recessed groove 551e may be provided. At this time, the fitting ring part 550a may extend to be round corresponding to a predetermined arc length and may be inserted into one side of the recessed groove 551e while the shape of the fitting ring part 550a matches the shape of the recessed groove 551e. That is, the holder unit 550 includes a hollow body 551d, a support means made of metal and integrally formed with a holder extension part 551, and the fitting ring part 550a provided at an outer side of the support means.

Here, the inner side of the fitting ring part 550a may be formed to have a volume that corresponds to or exceeds the width and depth at which the recessed groove 551e is open. Also, in a state in which the fitting ring part 550a is inserted into the recessed groove 551e while the shape of the fitting ring part 550a matches the shape of the recessed groove 551e, a diameter of the outermost boundary of the fitting ring part 550a may be formed to correspond to or exceed a diameter of the inner circumference 513 of the see-through body unit 510. At this time, the fitting ring part 550a may be made of rubber, silicone, a synthetic resin material such as LDPE that may be elastically deformed due to an external force. In some cases, like the holder unit 550, the fitting ring part 550a may be made of a metal material such as titanium.

Therefore, the state in which the holder unit 550 is fitted and coupled to one side of the see-through body unit 510 may be firmly maintained by a compressive force that is applied as the fitting ring part 550a is elastically deformed in correspondence with the inner circumference 513 of the see-through body unit 510, forcibly fitted, and then restored. Since the compressive force is formed to be larger than a coupling force between the coupling surface 521a and the inner circumferential portion of the holder unit 550, the holder unit 550 may be prevented from being separated due to removal of the first cap unit 520.

In the present disclosure, unless stated otherwise, the terms "include," "consist of," "provide," or "have" indicate that the corresponding element may be present. The terms indicate that other elements may be further included, instead of excluding other elements. Unless otherwise defined, all terms including technical or scientific terms used herein have the same meaning as commonly understood by one of ordinary skill in the art to which the present disclosure pertains. Terms, such as those defined in commonly used dictionaries, should be construed as having a meaning that is consistent with their meaning in the context of the related art and are not to be construed in an idealized or overly formal sense unless expressly so defined herein.

As described above, the present disclosure is not limited to the embodiments described above and may be modified and embodied by one of ordinary skill in the art to which the present disclosure pertains without departing from the scope of the claims of the present disclosure, and such modifications fall within the scope of the present disclosure

INDUSTRIAL APPLICABILITY

The present disclosure provides a packaging container for dental implants and may be applied to the industry for implants.

The invention claimed is:

1. A dental implant packaging container comprising:
a see-through body unit in which upper and lower sides are open to form an accommodation space so that a dental implant fixture is accommodated therein and which is made of a material through which ultraviolet (UV) light for surface modification passes;
a first cap unit which includes a hollow first cap body configured to cover an upper end portion of the accommodation space, a first fixing part protruding from a lower portion of the first cap body and having a coupling surface formed on an outer side portion, and a protruding part provided to protrude from the first fixing part so as to be inserted into an inner circumferential fastening groove of the fixture;
a hollow holder unit which has an outer circumferential portion coupled to an inner circumference of the see-through body unit and an inner circumferential portion coupled to the coupling surface to mediate the connection between the see-through body unit and the first cap unit; and
a second cap unit which includes a second fixing part fitted and coupled to a lower end portion of the see-through body unit and a base part provided on an inner side end of the second fixing part so that a lower end portion of the fixture is seated thereon.

2. The dental implant packaging container of claim 1, wherein:
the holder unit has an open central portion so that the fixture passes through the holder unit, and an outer circumferential portion of the holder unit is formed to protrude to be stepped outward in a radial direction and formed to be inclined inward in the radial direction toward a lower side so that a frictional fixing force is increased in a withdrawal direction; and
the first fixing part is formed in the shape of a bar positioned across a hollow portion of the first cap body and protrudes downward, and the coupling surface corresponds to a profile of an inner circumferential portion of the holder unit at either end of the bar-shaped first fixing part.

3. The dental implant packaging container of claim 1, wherein:
the holder unit protrudes downward from an inner side end of a hollow body configured to be seated on an upper end of the see-through body unit so as to be coupled to an inner circumference of the see-through body unit, and a fitting step part that expands to be stepped outward in a radial direction is formed on an inner circumference of a lower end portion of the holder unit; and
the dental implant packaging container further includes a bushing part that includes a ring-shaped body forcibly fitted to the fitting step part and bushing support parts provided to protrude downward from an inner side end of the ring-shaped body at UV transmission gaps formed at a plurality of sites in a circumferential direction.

4. The dental implant packaging container of claim 1, wherein a clearance portion is formed to be open in the shape of a slit at one side of the holder unit.

5. The dental implant packaging container of claim 1, wherein, in the first cap unit, first through-passages are formed in a semi-circular shape at a plurality of sites between the inner circumference of the first cap body and the first fixing part so that oxygen, which is converted to ozone to modify a surface of the fixture, is supplied.

6. The dental implant packaging container of claim 1, wherein:
on an edge of an upper surface of the base part, guide parts are provided to radially protrude at UV transmission gaps at a plurality of sites in a circumferential direction, and a corner portion that comes in point contact with an end portion of the fixture is formed on an inner side end of the guide part; and
a seating groove on which the lower end portion of the fixture is seated is formed on a bottom surface of an inner side of the base part that is surrounded by the guide parts.

7. The dental implant packaging container of claim 1, wherein the second cap unit further includes a hollow second cap body disposed on a lower end of the see-through body unit, and the second fixing part protrudes from an upper portion of the second cap body and has a fitting surface formed on an outer side portion of the second fixing part.

8. The dental implant packaging container of claim 7, wherein:
- the second fixing part is formed to cross a hollow of the second cap body and protrudes upward, and a separation space is formed between an outer side of a cutting surface, which is formed at a side surface of the second fixing part, and an inner circumference of the see-through body unit; and
- a second through-passage formed in the second cap unit communicates with the separation space and the accommodation space so that oxygen, which is converted to ozone to modify a surface of the fixture, is supplied.

9. The dental implant packaging container of claim 8, wherein, on the fitting surface, fitting protrusions, each having an upper surface portion formed to protrude to be inclined inward in the radial direction toward the upper side and a lower surface portion formed to be stepped, are provided at predetermined intervals at a plurality of sites in a vertical direction.

10. The dental implant packaging container of claim 1, wherein an end portion of the holder unit is provided to protrude while having UV transmission gaps formed at a plurality of sites in a circumferential direction.

11. The dental implant packaging container of claim 10, wherein the holder unit includes a holder extension part that protrudes downward from an inner side end of a hollow body configured to be seated on an upper end of the see-through body unit, so as to be inserted into an inner circumference of the see-through body unit and that has a recessed groove formed in the circumferential direction.

12. The dental implant packaging container of claim 11, wherein the holder unit includes a ring part that is provided in a ring shape, inserted into the recessed groove, and has an outer surface formed to protrude to be stepped outward in a radial direction and formed to be inclined inward in the radial direction so that a frictional fixing force is increased in a withdrawal direction.

13. The dental implant packaging container of claim 12, wherein:
- bushing support parts are provided to protrude downward at UV transmission gaps at a plurality of sites in a circumferential direction on an end portion of the holder unit, and the UV transmission gap is formed to be less than a diameter of an end portion of the fixture;
- on an end portion of the bushing support part, a support protrusion is formed to protrude inward in a radial direction so as to support an upper end portion of the fixture; and
- the ring part has open one side so as to be compatibly applied to an outer diameter of the holder extension part.

14. The dental implant packaging container of claim 11, wherein:
- the holder unit includes a fitting ring part which has an inner circumference inserted into one side of the recessed groove while the shape of the fitting ring part matches the shape of the recessed groove and which extends to be round corresponding to a predetermined arc length; and
- the arc length of the fitting ring part is formed to be in a range of 50% to 95% of the entire circumference of an inner circumferential portion of the recessed groove.

15. The dental implant packaging container of claim 14, wherein an expansion part is formed to expand and protrude outward in a radial direction from an upper side or lower side of an outer circumference of the fitting ring part so that, when the holder unit is coupled to an inner circumference of the see-through body unit, a frictional fixing force is increased in a withdrawal direction.

16. The dental implant packaging container of claim 1, wherein a grip groove portion is formed in a circumferential direction at one side or the other side of a marking part, which is provided on a cylindrical outer circumferential surface of the first cap body.

17. The dental implant packaging container of claim 1, wherein:
- a cutting surface is formed at a side surface portion of at least any one of the first fixing part and the second fixing part; and
- in at least any one of the first cap unit and the second cap unit, a through-passage is formed to pass through an end portion of the cutting surface so that oxygen, which is converted to ozone to modify a surface of the fixture, is supplied to the accommodation space.

18. The dental implant packaging container of claim 1, wherein, on the coupling surface, a catching protrusion is provided to protrude outward in a radial direction so as to be forcibly fitted to an inner circumference of the holder unit.

* * * * *